(12) United States Patent
Fagan et al.

(10) Patent No.: US 7,341,851 B2
(45) Date of Patent: Mar. 11, 2008

(54) IL-8 LIKE PROTEIN

(75) Inventors: Richard Fagan, London (GB); Christopher Benjamin Phelps, London (GB); Mark Douglas Davies, London (GB); Christine Power, Thoiry (FR)

(73) Assignee: Ares Trading, S.A., Aubonne (CH)

( * ) Notice: Subject to any disclaimer, the term of this patent is extended or adjusted under 35 U.S.C. 154(b) by 0 days.

(21) Appl. No.: 11/062,093

(22) Filed: Feb. 18, 2005

(65) Prior Publication Data

US 2006/0035339 A1 Feb. 16, 2006

(30) Foreign Application Priority Data

Aug. 19, 2002 (GB) ................................. 0219303.5

(51) Int. Cl.
*C07K 14/00* (2006.01)
*C07K 14/52* (2006.01)
*C07K 14/54* (2006.01)
*C12P 21/02* (2006.01)

(52) U.S. Cl. .................. 435/69.52; 435/69.5; 530/350; 530/351

(58) Field of Classification Search ..................... None
See application file for complete search history.

(56) References Cited

U.S. PATENT DOCUMENTS 5,194,596 A * 3/1993 Tischer et al. ............... 530/399
5,350,836 A * 9/1994 Kopchick et al. ........... 530/399
2001/0006681 A1 7/2001 Vico et al.

FOREIGN PATENT DOCUMENTS

WO  WO 98 31810  7/1998

OTHER PUBLICATIONS

Mukaida. Am J Physiol Lung Cell Mol Physiol. Apr. 2003;284(4):L566-77.*
NCBI Accession No. NP_957022, hypothetical protein LOC3937801 (Danio rerio).*
NCBI Accession No. NP_081175, Sssu72 RNA polymerase II CTD phosphatase homolog (*Mus musculus*).*
NCBI Accession No. BAE28662, unnamed protein product (*Mus musculus*).*
NCBI Accession No. AAH70675, MCG82356 protein (*Xenopus laevis*).*
NCBI Accession No. NP_990349, K60 protein (*Gallus gallus*).*
Benjamin et al., 1998, Development 125:1591-1598.*
Vukicevic et al. 1996, PNAS USA 93:9021-9026.*
Massague, 1987, Cell 49:437-8.*
Pilbeam et al., 1993, Bone 14:717-720.*
Skolnick et al. 2000, Trends in Biotech. 18:34-39.*
Bork. 2000, Genome Research 10:398-400.*
Doerks et al. 1998, Trends in Genetics 14:248-250.*
Smith et al. 1997, Nature Biotechnology 15:1222-1223.*
Brenner. 1999, Trends in Genetics 15:132-133.*
Bork et al. 1996, Trends in Genetics 12:425-427.*
Yoshimura et al., J Immunol May 15, 1991;146(10):3483-8.*
NCBI Accession No. AAH70675, MCG82356 protein (*Xenopus laevis*) (2002).*
NCBI Accession No. NP_990349, K60 protein (*Gallus gallus*) (2000).*
DATABASE EMBL 'Online! Standard; genomic DNA, HUM, 67683 BP, Feb. 21, 2002, Waterston R. H: "*Homo sapiens* BAC clone RP11-367M19 from 4, complete sequence" Database accession No. AC092438 XP0002264640.
Modi W S et al: "Isolation of novel GRO genes and a phylogenetic analysis of the CXC chemokine subfamily in mammals." Molecular Biology and Evolution, US, vol. 16, No. 2, Feb. 1999, pp. 180-193, XP002264638.
Modi W S et al: "Localization of the Human CXC Chemokine Subfamily on the Long Arm of Chromosome 4 Using Radiation Hybrids" Genomics, Academic Press, San Diego, US, vol. 47, No. 1, Jan. 1, 1998, pp. 136-139, XP004449320.
Strieter Robert M et al: "The functional role o the ELR motif in CXC chemokine-mediated angiogenesis" Journal of Biological Chemistry, American Society of Biological Chemists, Baltimore, MD, US, vol. 270, No. 45, 1995, pp. 27348-27357, XP002197946.
Hromas R et al: "Cloning of Brak, A Novel Divergent CXC Chemokine Preferentially Expressed in Normal Versus Malignant Cells" Biochemical and Biophysical Research Communications, Academic Press Inc. Orlando, FL, US, vol. 255, No. 3, 1999, pp. 703-706, XP001068272.
Clark-Lewis I et al: "Structural Requirements for Interleukin-8 Function Identified by Design of Analogs and CXC Chemokine Hybrids" Journal of Biological Chemistry, American Society of Biological Chemists, Baltimore, MD, US, vol. 269, No. 23, Jun. 10, 1994, pp. 16075-16081, XP001030753.
Smit A F: "Identification of a new abundant superfamily of mammalian LTR-transposons." Nucleic Acids Research. England Apr. 25, 1993, vol. 21, No. 8, pp. 1863-1872, XP008025704.

* cited by examiner

*Primary Examiner*—Gary B. Nickol
*Assistant Examiner*—Cherie M. Woodward
(74) *Attorney, Agent, or Firm*—Fromer Lawrence & Haug LLP; Thomas J. Kowalski; Angela M. Collison

(57) ABSTRACT

This present invention relates to a novel protein, termed INSP085, herein identified as an IL-8 like protein and to the use of this protein and nucleic acid sequence from the encoding genes in the diagnosis, prevention and treatment of disease.

3 Claims, 13 Drawing Sheets

FIG. 1

*Top 10 BLAST results searching with INSP085 against the NCBI non-redundant database.*

```
Query= INSP085
       (119 letters)

Database: ncbi-nr
   1,039,718 sequences; 328,277,582 total letters

Searching..................................................done
```

```
                                                                       Score      E
Sequences producing significant alignments:                           (bits)    Value ref|NP_035469.1| (NM_011339) small inducible cytokine subfamily ...     43     6e-04
emb|CAA75212.1| (Y14971) K60 protein [Gallus gallus] >gi|9280593...     40     0.005
sp|P36925|IL8_SHEEP Interleukin-8 precursor (IL-8) (CXCL8) >gi|5...     36     0.091
sp|P26894|IL8_PIG Interleukin-8 precursor (IL-8) (CXCL8) (Alveol...     35     0.12
sp|P79255|IL8_BOVIN Interleukin-8 precursor (IL-8) (CXCL8) >gi|1...     35     0.12
pir||A44253 alveolar macrophage chemotactic factor-I (AMCF-I) in...     35     0.12
ref|NP_006410.1| (NM_006419) small inducible cytokine B subfamil...     35     0.16
sp|P19874|IL8_RABIT Interleukin-8 precursor (IL-8) (CXCL8) (Neut...     35     0.16
emb|CAA43461.1| (X61151) interleukin-8 [Sus scrofa]                     35     0.16
ref|NP_000575.1| (NM_000584) interleukin 8 [Homo sapiens] >gi|12...     35     0.16
```

FIG. 2(i)

*Top 5 BLAST alignments from searching with INSP085 against the NCBI non-redundant database.*

```
>ref|NP_035469.1| (NM_011339) small inducible cytokine subfamily B, member 15 [Mus
     musculus]
sp|Q9WVL7|SZ15_MOUSE Small inducible cytokine B15 precursor (CXCL15) (Lungkine)
gb|AAD38079.1|AF082859_1 (AF082859) lungkine [Mus musculus]
     Length = 167

Score = 43.1 bits (100), Expect = 6e-04
Identities = 19/41 (46%), Positives = 25/41 (60%)

Query: 42  PKQVMRVGCQCIQTHSDFIPHQFIKNDQLIHKDPFCRRKEV 82
           P   + C CIQ HS+FIP + IKN +I +  +C RKEV
Sbjct: 22  PCDTQELRCLCIQEHSEFIPLKLIKNIMVIFETIYCNRKEV 62

>emb|CAA75212.1| (Y14971) K60 protein [Gallus gallus]
gb|AAF86485.1| (AF277660) CXC chemokine K60 [Gallus gallus]
     Length = 104
```

FIG. 2(ii)

```
Score = 40.0 bits (92), Expect = 0.005
Identities = 17/40 (42%), Positives = 24/40 (59%)

Query: 43  KQVMRVGCQCIQTHSDFIPHQFIKNDQLIHKDPFCRRKEV 82
           +  + CQCI+THS FI +FI+N  L   P C+  EV
Sbjct: 27  RSAIELRCQCIETHSKFIHPKFIQNVNLTPSGPHCKNVEV 66

>sp|P36925|IL8_SHEEP Interleukin-8 precursor (IL-8) (CXCL8)
 pir||S42496 interleukin 8 - sheep
 pir||I46997 interleukin-8 - sheep
 emb|CAA55115.1| (X78306) interleukin 8 [Ovis aries]
 gb|AAB33241.1| (S74436) interleukin-8; IL-8; neutrophil attractant/activation
     protein 1 [Ovis aries]
          Length = 101
```

FIG. 2(iii)

```
Score = 35.8 bits (81), Expect = 0.091
Identities = 19/56 (33%), Positives = 28/56 (49%)

Query:  50  CQCIQTHSDFIPHQFIKNDQLIHKDPFCRRKEVKHKVCVALIACIVEVKIVGQKIV 105
            CQCI+THS    +FIK  ++I   P C   E+ K+      C+    +   QK+V
Sbjct:  34  CQCIKTHSTPFHPKFIKELRVIESGPHCENSEIIVKLTNGKEVCLDPKEKWVQKVV 89
```

>sp|P26894|IL8_PIG Interleukin-8 precursor (IL-8) (CXCL8) (Alveolar macrophage chemotactic factor I) (AMCF-I)
pir||A53096 interleukin-8 precursor - pig
gb|AAA16616.1| (M86923) interleukin 8 [Sus scrofa]
gb|AAA92576.1| (M99367) alveolar macrophage-derived chemotactic factor-I [Sus scrofa]
Length = 103

FIG. 2(iv)

```
Score = 35.4 bits (80), Expect = 0.12
Identities = 19/56 (33%), Positives = 27/56 (47%)

Query: 50  CQCIQTHSDFIPHQFIKNDQLIHKDPFCRRKEVKHKKVCVALIACIVEVKIVGQKIV 105
           CQCI THS    +FIK ++I  P C  E+ K+    C+   +     QK+V
Sbjct: 34  CQCINTHSTPFHPKFIKELRVIESGPHCENSEIIVKLVNGKEVCLDPKEKWVQKVV 89

>sp|P79255|IL8_BOVIN Interleukin-8 precursor (IL-8) (CXCL8)
 gb|AAB37483.1| (S82598) interleukin-8; IL-8 [Bos taurus]
 gb|AAF37575.1|AF232704_1 (AF232704) interleukin 8 [Bos taurus]
          Length = 101

Score = 35.4 bits (80), Expect = 0.12
Identities = 19/56 (33%), Positives = 28/56 (49%)

Query: 50  CQCIQTHSDFIPHQFIKNDQLIHKDPFCRRKEVKHKKVCVALIACIVEVKIVGQKIV 105
           CQCI+THS    +FIK ++I  P C  E+ K+    C+   +     QK+V
Sbjct: 34  CQCIKTHSTPFHPKFIKELRVIESGPHCENSEIIVKLTNGNEVCLNPKEKWVQKVV 89
```

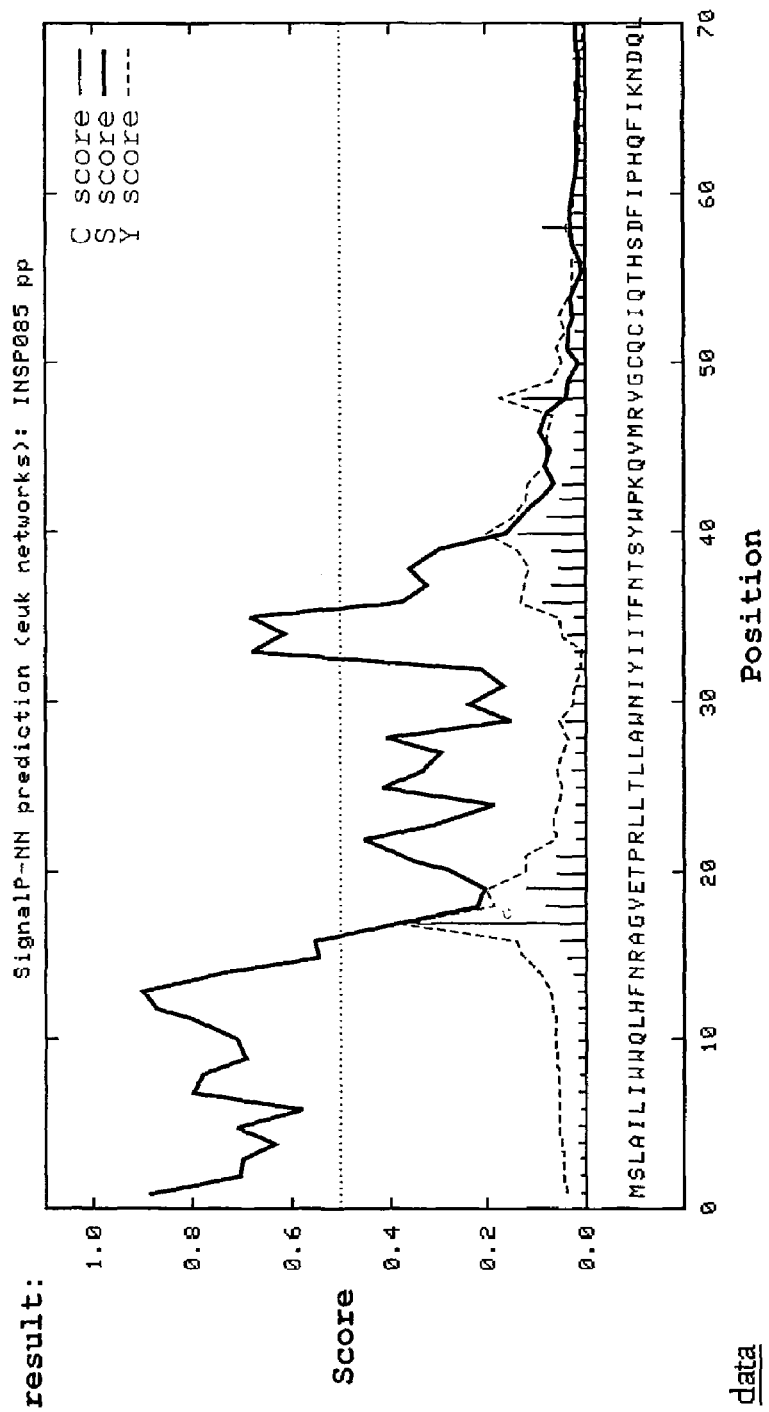
FIG. 3 Sig P cleavage site prediction for INSP085

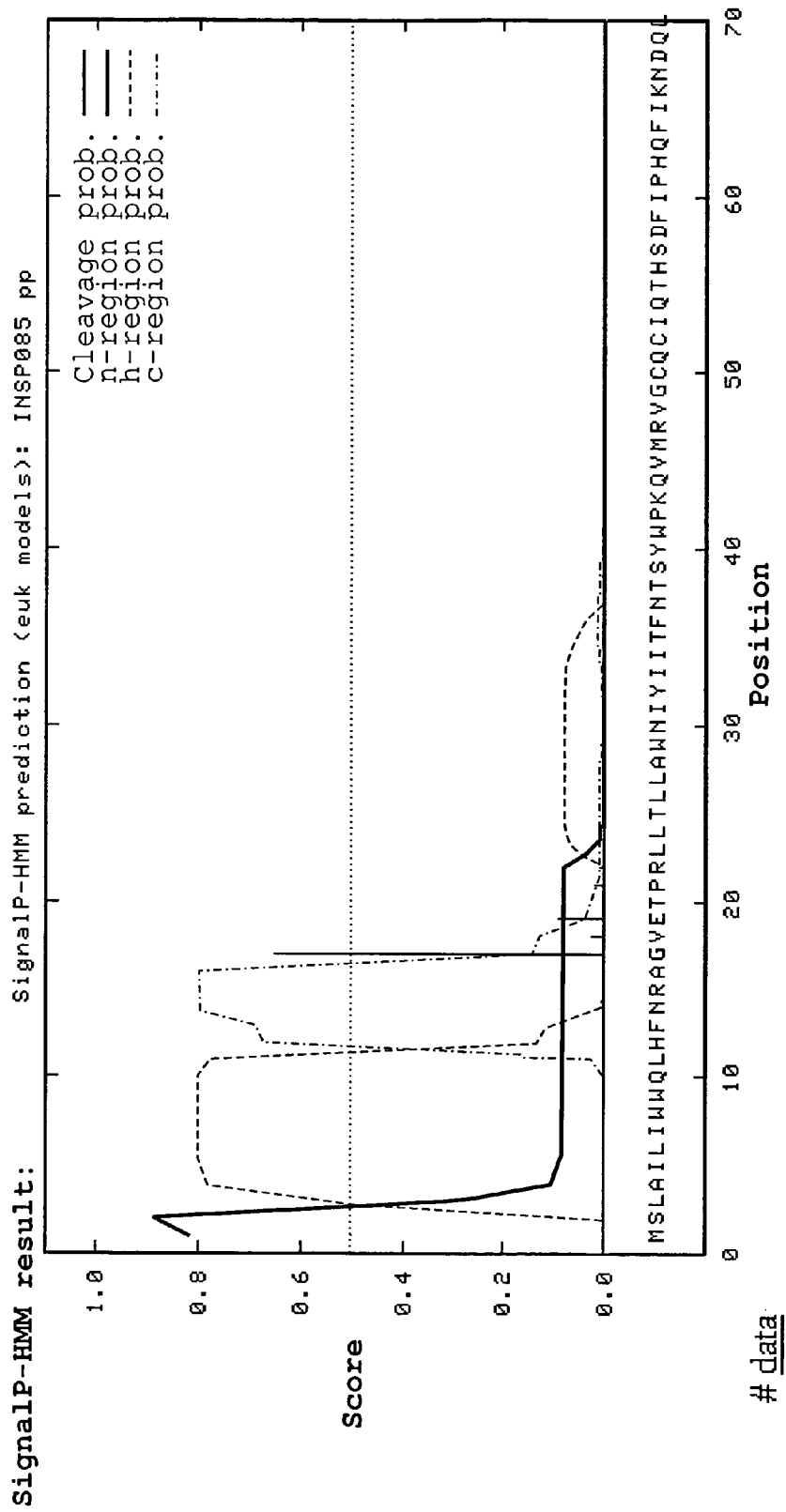
FIG. 4 Sig P peptide prediction for INSP085

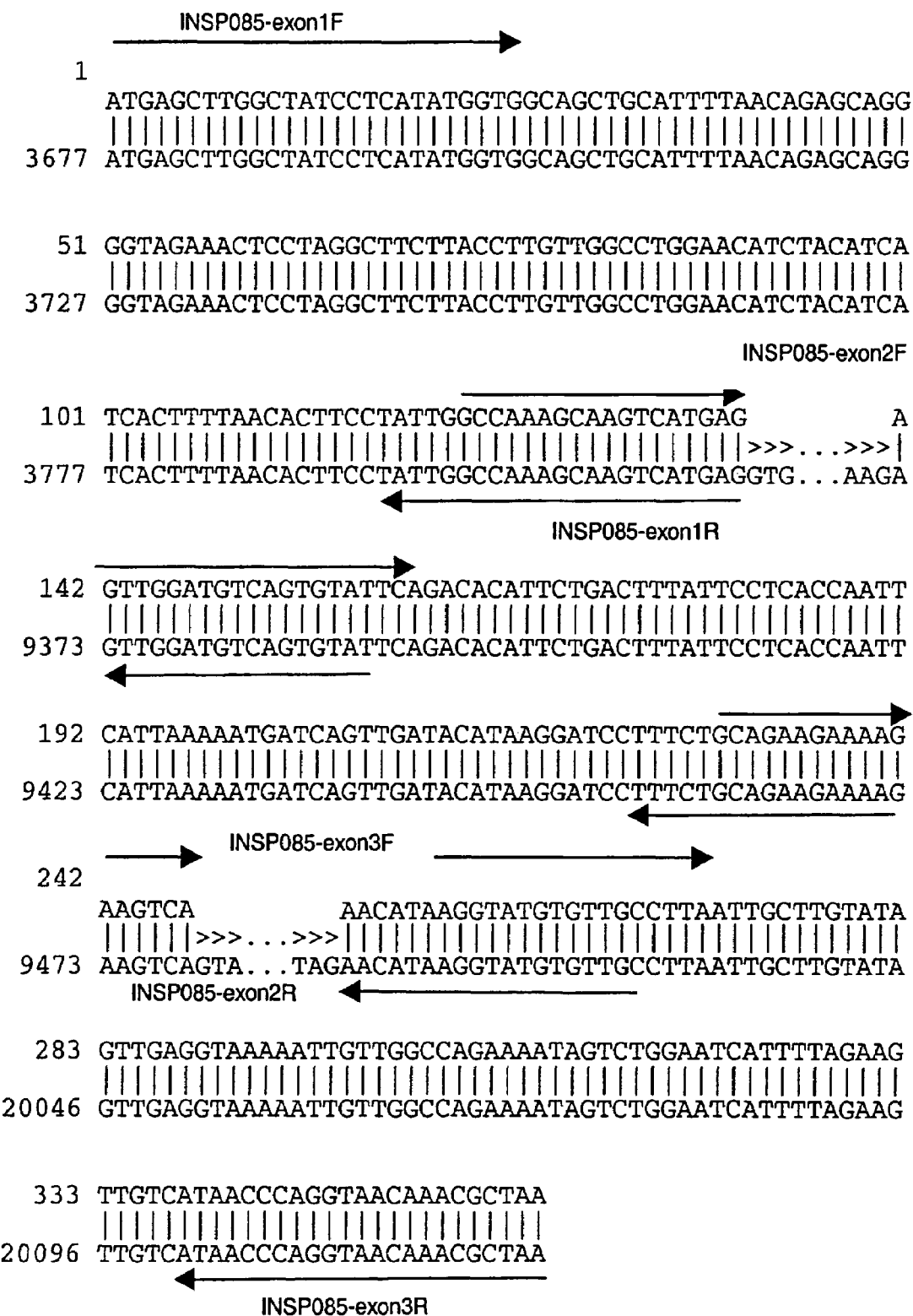
FIG. 5 INSP085 coding exon organization in genomic DNA and position of PCR primers

FIG. 6

Nucleotide sequence and translation of cloned INSP085 ORF. Predicted signal peptide is underlined.

```
  1  acaaaaaagc aggcttcgcc accatgagct tggctatcct catatggtgg
                                       m  s  l  a  i  l  i  w  w 51  cagctgcatt taacagagc aggggtagaa actcctaggc ttcttacctt
     q  l  h  f  n  r  a  g  v  e  t  p  r  l  l  t 101  gttggcctgg aacatctaca tcatcacttt taacacttcc tattggccaa
     l  l  a  w  n  i  y  i  i  t  f  n  t  s  y  w  p 151  agcaagtcat gagagttgga tgtcagtgta ttcagacaca ttctgacttt
     k  q  v  m  r  v  g  c  q  c  i  q  t  h  s  d  f 201  attcctcacc aattcattaa aaatgatcag ttgatacata aggatccttt
     i  p  h  q  f  i  k  n  d  q  l  i  h  k  d  p 251  ctgcagaaga aaagaagtca aacataaggt atgtgttgcc ttaattgctt
     f  c  r  r  k  e  v  k  h  k  v  c  v  a  l  i  a 301  gtatagttga ggtaaaaatt gttggccaga aaatagtctg gaatcatttt
     c  i  v  e  v  k  i  v  g  q  k  i  v  w  n  h  f 351  agaagttgtc ataacccagg taacaaacgc caccatcacc atcaccattg
     r  s  c  h  n  p  g  n  k  r  h  h  h  h  h  h 401  aaacccagct ttcttgtaca aagtggt
```

FIG. 7(i)

Map of pENTR-INSP085-6HIS

Molecule: pENTR-INSP085-6HIS-V1, 2642 bps DNA Circular

File Name: 13414-(pDONR201).cm5,

Description: pDONR201 with two recombination sites attP1 and attP2 called pENTR after cDNA insertion

| Type | Start | End | Name | Description |
|------|-------|-----|------|-------------|
| REGION | 13 | 2397 C | T1-T2 rrnB | |
| REGION | 122 | 29 C | attB1 | |
| GENE | 136 | 510 | INSP085-6HIS | |
| REGION | 518 | 614 | attB2 | |
| REGION | 661 | 638 C | pENTR-R | reverse primer |
| GENE | 737 | 1546 | Kan r | |
| GENE | 1667 | 2306 | ori | |
| REGION | 2639 | 21 | pENTR-F | forward primer |

FIG. 8(i)

Map of pEAK12d-INSP085-6HIS

Molecule: pEAK12d-INSP085-6HIS-V1, 7324 bps DNA Circular
File Name: 13413.cm5,

Description: pEAK12 DES with two recombination sites attR1 and attR2 between which the cDNA is inserted

| Type | Start | End | | Name | Description |
|---|---|---|---|---|---|
| REGION | 2 | 595 | | pmb-ori | |
| GENE | 596 | 1519 | | Amp | |
| REGION | 1690 | 2795 | | EF-1alpha | |
| REGION | 2703 | 2722 | | peak12-F | forward primer |
| REGION | 2855 | 2874 | | attB1 | |
| GENE | 2888 | 3262 | | INSP085-6HIS | |
| REGION | 3270 | 3291 | | attB2 | |
| REGION | 3298 | 3726 | | 'A | poly A/splice |
| REGION | 3412 | 3393 | C | peak12-R | reverse primer |
| GENE | 4345 | 3727 | C | PUR | PUROMYCIN |
| REGION | 4569 | 4346 | C | tK | tK promoter |
| REGION | 5064 | 4570 | C | Ori P | |
| GENE | 7116 | 5064 | C | EBNA-1 | |
| REGION | 7117 | 7316 | | sv40 | | ically of" and "consists essentially of" have the meaning
IL-8 LIKE PROTEIN

REFERENCE TO RELATED APPLICATIONS

This application is a continuation-in-part of International Patent Application PCT/GB2003/003646 filed Aug. 19, 2003 and published as WO 2004/016654 on Feb. 26, 2004, which claims priority from Great Britain Application 0219303.5 filed Aug. 19, 2002. Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, nonobvious, inventive, over the prior art, e.g., over documents cited herein or incorporated by reference herein. And, the terms "consists of" and "consisting of" have the meaning ascribed to them in U.S. Patent law; namely, that these terms are closed ended.

Il-Like Protein

This invention relates to a novel protein, termed INSP085, herein identified as a secreted. protein, in particular, as a member of the Interleukin (IL) 8-like chemokine family and to the use of this protein and nucleic acid sequence from the encoding gene in the diagnosis, prevention and treatment of disease.

All publications, patents and patent applications cited herein are incorporated in full by reference.

BACKGROUND

The process of drug discovery is presently undergoing a fundamental revolution as the era of functional genomics comes of age. The term "functional genomics" applies to an approach utilising bioinformatics tools to ascribe function to protein sequences of interest. Such tools are becoming increasingly necessary as the speed of generation of sequence data is rapidly outpacing the ability of research laboratories to assign functions to these protein sequences.

As bioinformatics tools increase in potency and in accuracy, these tools are rapidly replacing the conventional techniques of biochemical characterisation. Indeed, the advanced bioinformatics tools used in identifying the present invention are now capable of outputting results in which a high degree of confidence can be placed.

Various institutions and commercial organisations are examining sequence data as they become available and significant discoveries are being made on an on-going basis. However, there remains a continuing need to identify and characterise further genes and the polypeptides that they encode, as targets for research and for drug discovery.

INTRODUCTION

Secreted Proteins

The ability for cells to make and secrete extracellular proteins is central to many biological processes. Enzymes, growth factors, extracellular matrix proteins and signalling molecules are all secreted by cells. This is through fusion of a secretory vesicle with the plasma membrane. In most cases, but not all, proteins are directed to the endoplasmic reticulum and into secretory vesicles by a signal peptide. Signal peptides are cis-acting sequences that affect the transport of polypeptide chains from the cytoplasm to a membrane bound compartment such as a secretory vesicle. Polypeptides that are targeted to the secretory vesicles are either secreted into the extracellular matrix or are retained in the plasma membrane. The polypeptides that are retained in the plasma membrane will have one or more transmembrane domains. Examples of secreted proteins that play a central role in the functioning of a cell are cytokines, hormones, extracellular matrix proteins (adhesion molecules), proteases, and growth and differentiation factors. Description of some of the properties of these proteins follows.

Chemokines

These signalling molecules are distinct from cytokines and are responsible for inducing chemotaxis or directed migration. They are highly specific, a fact which is illustrated by the fact that IL-8 is chemotactic to granulocytes but not monocytes. Chemokines contain four conserved cysteine residues and are divided into three families, α (CXC), β (CC) and γ (C), based on the position of conserved cysteine residues. If the first two cysteines are separated by another amino acid, then the chemokine is a member of the α family, while the first two cysteine residues are next to each other in the β family members. Members of the γ family only have one cysteine residue, rather than two, in their N-terminus. In the a and β families, disulphide bonds are formed between the first and third and the second and fourth residues.

Specificity of chemokines depends on the presence of specific receptors on cell surfaces. Chemokines have been shown to play a role in the migration of leukocytes. Upon activation, remodeling of the cytoskeleton of leukocytes is induced allowing the cell to flatten and pass from an intravascular space into a tissue space. Interaction of chemokines with seven-transmembrane G-protein coupled receptors leads to rapid accumulation of intracellular free calcium in the responding cells. This mobilisation is critical for chemotaxis, respiratory burst and upregulation of adhesive interactions of leukocytes. Chemokines have also been shown to regulate the expression of adhesion molecules on neutrophils, monocytes, lymphocytes and eosinophils. For example, MIP-1α and RANTES cause adhesion of monocytes to endothelium while MIP-1β induces $CD8^+$ T-cell adhesion to endothelium.

Increasing knowledge of these domains is therefore of extreme importance in increasing the understanding of the underlying pathways that lead to the disease states and associated disease states mentioned above, and in developing more effective gene and/or drug therapies to treat these disorders.

THE INVENTION

The invention is based on the discovery that the INSP085 polypeptide is an IL-8 like chemokine.

In one embodiment of the first aspect of the invention, there is provided a polypeptide which:
(i) comprises the amino acid sequence as recited in SEQ ID NO:2, SEQ ID NO:4, SEQ ID NO:6, SEQ ID NO:8, SEQ ID NO10 and/or SEQ ID NO:12;
(ii) is a fragment thereof which functions as a member IL-8 like chemokine family, or has an antigenic determinant in common with the polypeptides of (i); or
(iii) is a functional equivalent of (i) or (ii).

Preferably, the polypeptide according to this first aspect of the invention:
(i) comprises the amino acid sequence as recited in SEQ ID NO:8, SEQ ID NO:10 and/or SEQ ID NO:12;
(ii) is a fragment thereof which functions as a member of the IL-8 like chemokine family, or has an antigenic determinant in common with the polypeptides of (i); or
(iii) is a functional equivalent of (i) or (ii).

According to a second embodiment of this first aspect of the invention, there is provided a polypeptide which:
(i) consists of the amino acid sequence as recited in SEQ ID NO:2, SEQ ID NO:4, SEQ ID NO:6, SEQ ID NO:8, SEQ ID NO: 10 and/or SEQ ID NO: 12;
(ii) is a fragment thereof which functions as a member of the IL-8 like chemokine family, or having an antigenic determinant in common with the polypeptides of (i); or
(iii) is a functional equivalent of (i) or (ii).

The polypeptide having the sequence recited in SEQ ID NO:2 is referred to hereafter as "INSP085 exon 1 polypeptide". The polypeptide having the sequence recited in SEQ ID NO:4 is referred to hereafter as "INSP085 exon 2 polypeptide". The polypeptide having the sequence recited in SEQ ID NO:6 is referred to hereafter as "INSP085 exon 3 polypeptide". The polypeptide having the sequence recited in SEQ ID NO:8 is referred to hereafter as the "INSP085 polypeptide".

The term "INSP085 polypeptides" as used herein includes polypeptides comprising the INSP085 exon 1 polypeptide, the INSP085 exon 2 polypeptide, the INSP085 exon 3 polypeptide and the INSP085 polypeptide.

Although the Applicant does not wish to be bound by this theory, it is postulated that the first 16 amino acids of the INSP085 exon 1 polypeptide form a signal peptide.

The INSP085 exon 1 and full length INSP085 polypeptide sequences without this postulated signal sequence are recited in SEQ ID NO:10 and SEQ ID NO:12 respectively.

The polypeptide having the sequence recited in SEQ ID NO:10 is referred to hereafter as "the INSP085 exon 1 mature polypeptide". The polypeptide having the sequence recited in SEQ ID NO:12 is referred to hereafter as "the INSP085 mature polypeptide".

By "functions as a member of the IL-8 like chemokine family" we refer to polypeptides that comprise amino acid sequence or structural features that can be identified as conserved features within the polypeptides of the IL-8 like chemokine family, such that the polypeptide's interaction with ligand is rot substantially affected detrimentally in comparison to the function of the full length wild type polypeptide. In particular, we refer to the presence of cysteine residues in specific positions within the polypeptide that allow the formation of intra-domain disulphide bonds.

Studies on structure-activity relationships indicate that chemokines bind and activate receptors by making use of the amino-terminal region. Proteolytic digestion, mutagenesis, or chemical modifications directed to amino acids in this region can generate compounds having antagonistic activity (Loetscher P and Clark-Lewis I, J Leukoc Biol, 69: 881-884, 2001 Lambeir A, et al. J Biol Chem, 276: 2983 9-29845, 2001, Proost P, et al. Blood, 98 (13):3554-3561, 2001). Thus, antagonistic molecules resulting from specific modifications (deletions, non-conservative substitutions) of one or more residues in the amino-terminal region or in other regions of the corresponding chemokine are considered having therapeutic potential for inflammatory and autoimmune diseases (WO 02/28419; WO 00/27880; WO 99/33989; Schwarz MK and Wells TN, Curr Opin Chem Biol, 3: 407-17, 1999). Therefore, a farther object of the present patent application is represented by such kind of antagonists generated by modifying the polypeptides of the invention.

The therapeutic applications of the polypeptides of the invention and of the related reagents can be evaluated (in terms of safety, pharmacokinetics and efficacy) by the means of the in vivo/in vitro assays making use of animal cell, tissues and models (Coleman RA et al., Drug Discov Today, 6: 1116-1126, 2001; Li AP, Drug Discos Today, 6: 357-366, 2001; Methods Mol. Biol vol. 138, "Chemokines Protocols", edited by Proudfoot A I et al., Humana Press Inc., 2000; Methods Enzymol, vol. 287 and 288, Academic Press, 1997), or by the means of in silico/computational approaches (Johnson DE and Wolfgang GH, Drug Discov Today, 5: 445-454, 2000), known for the validation of chemokines and other biological products during drug discovery and preclinical development.

The present application discloses novel chemokine-like polypeptides and a series of related reagents that may be useful, as active ingredients in pharmaceutical compositions appropriately formulated, in the treatment or prevention of diseases such as cell proliferative disorders, autoimmune/inflammatory disorders, cardiovascular disorders, neurological disorders, developmental disorders, metabolic disorder, infections and other pathological conditions. In particular, given the known properties of chemokines, the disclosed polypeptides and reagents should address conditions involving abnormal or defective cell migration. Non-limitative examples of such conditions are the following: arthritis, rheumatoid arthritis (RA), psoriatic arthritis, osteoartritis, systemic lupus erythematosus (SLE), systemic sclerosis, scleroderma, polymyositis, glomerulonephritis, fibrosis, lung fibrosis and inflammation, allergic or hypersensitvity diseases, dermatitis, asthma, chronic obstructive pulmonary disease (COPD), inflammatory bowel disease (IBD), Crohn's disease, ulcerative colitis, multiple sclerosis, septic shock, HIV infection, transplant rejection, wound healing, metastasis, endometriosis, hepatitis, liver fibrosis, cancer, analgesia, and vascular inflammation related to atherosclerosis.

Several assays have been developed for testing specificity, potency, and efficacy of chemokines using cell cultures or animal models, for example in vitro chemotaxis assays (Proudfoot A, et al. J Biol Chem 276: 10620-10626, 2001; Lusti-Narasimhan M et al., J Biol Chem, 270: 2716-21, 1995), or mouse ear swelling (Garrigue JL et al., Contact Dermatitis, 30: 231-7, 1994). Many other assays and technologies for generating useful tools and products (antibodies, transgenic animals, radiolabeled proteins, etc.) have been described in reviews and books dedicated to chemokines (Methods Mol. Biol vol. 138, "Chemokines Protocols", edited by Proudfoot AI et al., Humana Press Inc., 2000; Methods Enzymol, vol. 287 and 288, Academic Press, 1997), and can be used to verify, in a more precise manner, the biological activities of the chemokine-like polypeptides of the invention and related reagents in connection with possible therapeutic or diagnostic methods and uses.

The following in vitro cell-based tri-replicas assays measure the effects of the protein of the invention on cytokine secretion induced by Concanavalin A (Con A) acting on different human peripheral blood mononuclear cells (hPBMC) cells as measured by a cytokine bead array (CBA) assay for IL-2, IFN-γ, TNF-α, IL-5, IL-4 and IL-10 such as the Human Th1/Th2 Cytokine CBA kit (Becton-Dickinson).

The optimal conditions are 100 000 cells/well in 96-well plates and 100 µl final in 2% glycerol. The optimal concentration of mitogen (ConA) is 5 ng/ml. The optimal time for the assay is 48 h. The read-out choice is the CBA.

1 Purification of Human PBMC from a Buffer Coat

The buffy coat 1 to 2 is diluted with DMEM. 25 ml of diluted blood was thereafter slowly added onto a 15 ml layer of Ficoll in a 50 ml Falcon tube, and tubes are centrifuged (2000 rpm, 20 min, at RT without brake). The interphase (ring) is then collected and the cells are washed with 25 ml of DMEM followed by a centrifuge step (1200 rpm, 5 min). This procedure is repeated three times. A buffy coat gives approximately $600 \times 10^6$ total cells.

2 Screening

80 µl of $1.25 \times 10^6$ cells/ml are diluted in DMEM±2.5% Human Serum+1% L-Glutamine+1% Penicillin-Streptomycin and. thereafter added to a 96 well microtiter plate.

10 µl are added per well (one condition per well): Proteins were diluted in PBS+20% Glycerol (the final dilution of the proteins is 1/10).

10 µl of the ConA Stimulant (50 µg/ml) are then added per well (one condition per well—the final concentration of ConA is 5 µg/ml)

After 48 h, cell supernatants are collected and human cytokines are measured by Human Th1/Th2 Cytokine CBA Kit BECTON-DICKISON®.

3 CBA Analysis (for more details, refer to the manufacturer's instructions in the CBA kit)

i) Preparation of Mixed Human Th1/Th2 Capture Beads

The number of assay tubes that are required for the experiment are determined.

Each capture bead suspension is vigorously vortexed for a few seconds before mixing. For each assay to be analysed, 10 µl aliquot of each capture bead are added into a single tube labelled "mixed capture beads". The Bead mixture is thoroughly vortexed.

ii) Preparation of Test Samples

Supernatants are diluted (1:4) using the Assay Diluent (20 µl of supernatants+60 µl of Assay Diluent). The sample dilution is then mixed before transferring samples into a 96 well conical bottomed microtiter plate (Nunc).

iii) Human Th1/Th2 Cytokine CBA Assay Procedure

50 µl of the diluted supernatants are added into a 96 well conical bottomed microtiter plate (Nunc). 50 µl of the mixed capture beads are added followed by 50 µl addition of the Human Th1/Th2 PE Detection Reagent. The plate is then incubated for 3 hours at RT and protected from direct exposure to light followed by centrifugation at 1500 rpm for 5 minutes. The supernatant is then carefully discarded. In a subsequent step, 200 µl of wash buffer are twice added to each well, centrifuged at 1500 rpm for 5 minutes and supernatant carefully discarded. 130 µl of wash buffer are thereafter added to each well to resuspended the bead pellet.

The samples are finally analysed on a flow cytometer. The data are than analysed using the CBA Application Software, Activity Base and Microsoft Excel software.

From the read-out of the assay it can be evaluated whether in vitro, the protein of the invention has a consistent inhibitory effect on all cytokines tested (IFN-γ, TNF-α, IL-2, IL-4, IL-5, IL-10).

Moreover, based on the EC50 value, it can be easily evaluated which cytokine is inhibited the most and then derive the specific auto-immune/inflammatory disease, which is known to be particularly linked to that cytokine.

In a second aspect, the invention provides a purified nucleic acid molecule which encodes a polypeptide of the first aspect of the invention.

Preferably, the purified nucleic acid molecule comprises the nucleic acid sequence as recited in SEQ ID NO:1 (encoding the INSP085 exon 1 polypeptide), SEQ ID NO:3 (encoding the INSP085 exon 2 polypeptide), SEQ ID NO:5 (encoding the INSP085 exon 3 polypeptide) and/or SEQ ID NO:7 (encoding the INSP085 polypeptide) or is a redundant equivalent or fragment of any one of these sequences.

The invention further provides that the purified nucleic acid molecule consists of the nucleic acid sequence as recited in SEQ ID NO:1 (encoding the INSP085 exon 1 polypeptide), SEQ ID NO:3 (encoding the INSP085 exon 2 polypeptide), SEQ ID NO:5 (encoding the INSP085 exon 3 polypeptide) and/or SEQ ID NO:7 (encoding the INSP085 polypeptide) or is a redundant equivalent or fragment of any one of these sequences.

The polypeptide having the sequence recited in SEQ ID NO:9 is referred to hereafter as "the INSP085 exon 1 mature nucleotide sequence" and encodes the INSP085 exon 1 mature polypeptide. The polypeptide having the sequence recited in SEQ ID NO:1 is referred to hereafter as "the INSP085 mature nucleotide sequence" and encodes the INSP085 mature polypeptide.

In a third aspect, the invention provides a purified nucleic acid molecule which hybridizes under high stringency conditions with a nucleic acid molecule of the second aspect of the invention.

In a fourth aspect, the invention provides a vector, such as an expression vector, that contains a nucleic acid molecule of the second or third aspect of the invention.

In a fifth aspect, the invention provides a host cell transformed with a vector of the fourth aspect of the invention.

In a sixth aspect, the invention provides a ligand which binds specifically to protein members of the IL-8 like chemokine family of the first aspect of the invention. Preferably, the ligand inhibits the function of a polypeptide of the first aspect of the invention which is a member of the IL-8 like chemokine family or proteins. Ligands to a polypeptide according to the invention may come in various forms, including natural or modified substrates, enzymes, receptors, small organic molecules such as small natural or synthetic organic molecules of up to 2000 Da, preferably 800 Da or less, peptidomimetics, inorganic molecules, peptides, polypeptides, antibodies, structural or functional mimetics of the aforementioned.

In a seventh aspect, the invention provides a compound that is effective to alter the expression of a natural gene which encodes a polypeptide of the first aspect of the invention or to regulate the activity of a polypeptide of the first aspect of the invention.

A compound of the seventh aspect of the invention may either increase (agonies) or decrease (antagonize) the level of expression of the gene or the activity of the polypeptide.

Importantly, the identification of the function of the INSP085 polypeptides allows for the design of screening methods capable of identifying compounds that are effective in the treatment and/or diagnosis of disease. Ligands and compounds according to the sixth and seventh aspects of the invention may be identified using such methods. These methods are included as aspects of the present invention.

In an eighth aspect, the invention provides a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention or a compound of the seventh aspect of the invention, for use in therapy or diagnosis of diseases in which members of the IL-8 like chemokine family are implicated. Such diseases may include cell proliferative disorders, including neoplasm, melanoma, lung, colorectal, breast, pancreas, head and neck and other solid tumours; myeloproliferative disorders, such as leukemia, non-Hodgkin lymphoma, leukopenia, thrombocytopenia, angiogeneis disorder, Kaposis' sarcoma; autoimmune/inflammatory disorders, including allergy, inflammatory bowel disease, arthritis, psoriasis and respiratory tract inflammation, asthma, and organ transplant rejection; cardiovascular disorders, including hypertension, oedema, angina, atherosclerosis, thrombosis, sepsis, shock, reperfusion injury, and ischemia; neurological disorders including central nervous system disease, Alzheimer's disease, brain injury, amyotrophic lateral sclerosis, and pain; developmental disorders; metabolic disorders including diabetes mellitus, osteoporosis, and obesity, AIDS and renal disease; infections including viral infection, bacterial infection, fungal infection and parasitic infection and other pathological conditions. Preferably, the disease is one in which the IL-8 like chemokine family is implicated, such as arthritis, rheumatoid arthritis (RA), psoriatic arthritis, osteoarthritis, systemic lupus erythematosus (SLE), systemic sclerosis, scleroderma, polymyositis, glomerulonephritis, fibrosis, lung fibrosis and inflammation, allergic or hypersensitvity diseases, dermatitis, asthma, chronic obstructive pulmonary disease (COPD), inflammatory bowel disease (IBD), Crohn's diseases, ulcerative colitis, multiple sclerosis, septic shock, HIV infection, transplant rejection, wound healing, metastasis, endometriosis, hepatitis, liver fibrosis, cancer, analgesia, and vascular inflammation related to atherosclerosis. These molecules may also by used in the manufacture of a medicament for the treatment of such diseases. These molecules may also be used in contraception or for the treatment of reproductive disorders including infertility.

In a ninth aspect, the invention provides a method of diagnosing a disease in a patient, comprising assessing the level of expression of a natural gene encoding a polypeptide of the first aspect of the invention or the activity of a polypeptide of the first aspect of the invention in tissue from said patient and comparing said level of expression or activity to a control level, wherein a level that is different to said control level is indicative of disease. Such a method will preferably be carried out in vitro. Similar methods may be used for monitoring the therapeutic treatment of disease in a patient, wherein altering the level of expression or activity of a polypeptide or nucleic acid molecule over the period of time towards a control level is indicative of regression of disease.

A preferred method for detecting polypeptides of the first aspect of the invention comprises the steps of: (a) contacting a ligand, such as an antibody, of the sixth aspect of the invention with a biological sample under conditions suitable for the formation of a ligand-polypeptide complex; and (b) detecting said complex.

A number of different such methods according to the ninth aspect of the invention exist, as the skilled reader will be aware, such as methods of nucleic acid hybridization with short probes, point mutation analysis, polymerase chain reaction (PCR) amplification and methods using antibodies to detect aberrant protein levels. Similar methods may be used on a short or long term basis to allow therapeutic treatment of a disease to be monitored in a patient. The invention also provides kits that are useful in these methods for diagnosing disease.

In a tenth aspect, the invention provides for the use of a polypeptide of the first aspect of the invention as an IL-8 like chemokine. Suitable uses of the polypeptides of the invention as IL-8 like chemokine proteins include use as a regulator of cellular growth, metabolism or differentiation, use as part of a receptor/ligand pair and use as a diagnostic marker for a physiological or pathological condition selected from the list given above.

In an eleventh aspect, the invention provides a pharmaceutical composition comprising a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, in conjunction with a pharmaceutically-acceptable carrier.

In a twelfth aspect, the present invention provides a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, for use in the manufacture of a medicament for the diagnosis or treatment of a disease.

In a thirteenth aspect, the invention provides a method of treating a disease in a patient comprising administering to the patient a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention.

For diseases in which the expression of a natural gene encoding a polypeptide of the first aspect of the invention, or in which the activity of a polypeptide of the first aspect of the invention, is lower in a diseased patient when compared to the level of expression or activity in a healthy patient, the polypeptide, nucleic acid molecule, ligand or compound administered to the patient should be an agonist. Conversely, for diseases in which the expression of the natural gene or activity of the polypeptide is higher in a diseased patient when compared to the level of expression or activity in a healthy patient, the polypeptide, nucleic acid molecule, ligand or compound administered to the patient should be an antagonist. Examples of such antagonists include antisense nucleic acid molecules, ribozymes and ligands, such as antibodies.

In a fourteenth aspect, the invention provides transgenic or knockout non-human animals that have been transformed to express higher, lower or absent levels of a polypeptide of the first aspect of the invention. Such transgenic animals are very useful models for the study of disease and may also be used in screening regimes for the identification of compounds that are effective in the treatment or diagnosis of such a disease.

A summary of standard techniques and procedures which may be employed in order to utilise the invention is given below. It will be understood that this invention is not limited to the particular methodology, protocols, cell lines, vectors and reagents described. It is also to be understood that the terminology used herein is for the purpose of describing particular embodiments only and it is not intended that this terminology should limit the scope of the present invention. The extent of the invention is limited only by the terms of the appended claims.

Standard abbreviations for nucleotides and amino acids are used in this specification.

The practice of the present invention will employ, unless otherwise indicated, conventional techniques of molecular biology, microbiology, recombinant DNA technology and immunology, which are within the skill of those working in the art.

Such techniques are explained fully in the literature. Examples of particularly suitable texts for consultation include the following: Sambrook Molecular Cloning; A Laboratory Manual, Second Edition (1989); DNA Cloning, Volumes I and II (D. N Glover ed. 1985); Oligonucleotide Synthesis (M. J. Gait ed. 1984); Nucleic Acid Hybridization (B. D. Hames & S. J. Higgins eds. 1984); Transcription and Translation (B. D. Hames & S. J. Higgins eds. 1984); Animal Cell Culture (R I. Freshney ed. 1986); Immobilized Cells and Enzymes (IRL Press, 1986); B. Perbal, A Practical Guide to Molecular Cloning (1984); the Methods in Enzymology series (Academic Press, Inc.), especially volumes 154 & 155; Gene Transfer Vectors for Mammalian Cells (J. H. Miller and M. P. Calos eds. 1987, Cold Spring Harbor Laboratory); Immunochemical Methods in Cell and Molecular Biology (Mayer and Walker, eds. 1987, Academic Press, London); Scopes, (1987) Protein Purification: Principles and Practice, Second Edition (Springer Verlag, N.Y.); and Handbook of Experimental Immunology, Volumes I-IV (D. M. Weir and C. C. Blackwell eds. 1986).

As used herein, the term "polypeptide" includes any peptide or protein comprising two or more amino acids joined to each other by peptide bonds or modified peptide bonds, i.e. peptide isosteres. This term refers both to short chains (peptides and oligopeptides) and to longer chains (proteins).

The polypeptide of the present invention may be in the form of a mature protein or may be a pre-, pro- or preproprotein that can be activated by cleavage of the pre-, pro- or prepro-portion to produce an active mature polypeptide. In such polypeptides, the pre-, pro- or prepro-sequence may be a leader or secretory sequence or may be a sequence that is employed for purification of the mature polypeptide sequence.

The polypeptide of the first aspect of the invention may form part of a fusion protein. For example, it is often advantageous to include one or snore additional amino acid sequences which may contain secretory or leader sequences, pro-sequences, sequences which aid in purification, or sequences that confer higher protein stability, for example during recombinant production. Alternatively or additionally, the mature polypeptide may be fused with another compound, such as a compound to increase the half-life of the polypeptide (for example, polyethylene glycol).

Polypeptides may contain amino acids other than the 20 gene-encoded amino acids, modified either by natural processes, such as by post-translational processing or by chemical modification techniques which are well known in the art. Among the known modifications which may commonly be present in polypeptides of the present invention are glycosylation, lipid attachment, sulphation, gamma-carboxylation, for instance of glutamic acid residues, hydroxylation and ADP-ribosylation. Other potential modifications include acetylation, acylation, amidation, covalent attachment of flavin, covalent attachment of a haeme moiety, covalent attachment of a nucleotide or nucleotide derivative, covalent attachment of a lipid derivative, covalent attachment of phosphatidylinositol, cross-linking, cyclization, disulphide bond formation, demethylation, formation of covalent cross-links, formation of cysteine, formation of pyrroglutamate, formylation, GPI anchor formation, iodination, methylation, myristoylation, oxidation, proteolytic processing, phosphorylation, prenylation, racemization, selenoylation, transfer-RNA mediated addition of amino acids to proteins such as arginylation, and ubiquitination.

Modifications can occur anywhere in a polypeptide, including the peptide backbone, the amino acid side-chains and the amino or carboxyl termini. In fact, blockage of the amino or carboxyl terminus in a polypeptide, or both, by a covalent modification is common in naturally-occurring and synthetic polypeptides and such modifications may be present in polypeptides of the present invention.

The modifications that occur in a polypeptide often will be a function of how the polypeptide is made. For polypeptides that are made recombinantly, the nature and extent of the modifications in large part will be determined by the post-translational modification capacity of the particular host cell and the modification signals that are present in the amino acid sequence of the polypeptide in question. For instance, glycosylation patterns vary between different types of host cell.

The polypeptides of the present invention can be prepared in any suitable manner. Such polypeptides include isolated naturally-occurring polypeptides (for example purified from cell culture), recombinantly-produced polypeptides (including fusion proteins), synthetically-produced polypeptides or polypeptides that are produced by a combination of these methods.

The functionally-equivalent polypeptides of the first aspect of the invention may be polypeptides that are homologous to the INSP085 polypeptides. Two polypeptides are said to be "homologous", as the term is used herein, if the sequence of one of the polypeptides has a high enough degree of identity or similarity to the sequence of the other polypeptide. "Identity" indicates that at any particular position in the aligned sequences, the amino acid residue is identical between the sequences. "Similarity" indicates that, at any particular position in the aligned sequences, the amino acid residue is of a similar type between the sequences. Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Giribskov, M. and Devereux, J., eds., M Stockton Press, New York, 1991).

Homologous polypeptides therefore include natural biological variants (for example, allelic variants or geographical variations within the species from which the polypeptides arc derived) and mutants (such as mutants containing amino acid substitutions, insertions or deletions) of the INSP085 polypeptides. Such mutants may include polypeptides in which one or more of the amino acid residues are substituted with a conserved or non-conserved amino acid residue (preferably a conserved amino acid residue) and such substituted amino acid Residue may or may not be one encoded by the genetic code. Typical such substitutions are among Ala, Val, Leu and Ile; among Ser and Thr; among the acidic residues Asp and Glu; among Asn and Gln; among the basic residues Lys and Arg; or among the aromatic residues Phe and Tyr. Particularly preferred are variants in which several, i.e. between 5 and 10, 1 and 5, 1 and 3, 1 and 2 or just 1 amino acids are substituted, deleted or added in any combination. Especially preferred are silent substitutions, additions and deletions, which do not alter the properties and activities of the protein. Also especially preferred in this regard are conservative substitutions. Such mutants also include polypeptides in which one or more of the amino acid residues includes a substituent group.

Typically, greater than 30% identity between two polypeptides is considered to be an indication of functional equivalence. Preferably, functionally equivalent polypeptides of the first aspect of the invention have a degree of sequence identity with the INSP085 polypeptide, or with active fragments thereof, of greater than 80%. More preferred polypeptides have degrees of identity of greater than 85%, 90%, 95%, 98% or 99%, respectively.

The functionally-equivalent polypeptides of the first aspect of the intention may also be polypeptides which have been identified using one or more techniques of structural alignment. For example, the Inphannatica Genome Threader technology that forms one aspect of the search tools used to generate the Biopendium™ search database may be used (see PCT application WO 01/69507) to identify polypeptides of presently-unknown function which, while having low sequence identity as compared to the INSP085 polypeptides, are predicted to be members of the IL-8 like chemokine family, by virtue of sharing significant structural homology with the ISP085 polypeptide sequence. By "significant structural homology" is meant that the Inpharmatica Genome Threader predicts two proteins to share structural homology with a certainty of 10% and above.

The polypeptides of the first aspect of the invention also include fragments of the INSP085 polypeptides and fragments of the functional equivalents of the IN SP085 polypeptides, provided that those fragments are members of the IL-8 like chemokine family or have an antigenic determinant in common with the INSP085 polypeptides.

As used herein, the term "fragment" refers to a polypeptide having an amino acid sequence that is the same as part, but not all, of the amino acid sequence of the INSP085 polypeptide or one of their functional equivalents. The fragments should comprise at least n consecutive amino acids from the sequence and, depending on the particular sequence, n preferably is 7 or more (for example, 8, 10, 12, 14, 16, 18, 20 or more). Small fragments may form an antigenic determinant.

Fragments of the full length INSP085 polypeptides may consist of combinations of 2 or 3 of neighbouring exon sequences in the INSP085 polypeptide sequences, respectively. For example, such combinations include exons 1 and 2, 2 and 3 or 1, 2 and 3. Such fragments are included in the present invention.

Such fragments may be "free-standing", i.e. not part of or fused to other amino acids or polypeptides, or they may be comprised within larger polypeptide of which they form a part or region. When comprised within a larger polypeptide, the fragment of the invention most preferably forms a single continuous region. For instance, certain preferred embodiments relate to a fragment having a pre- and/or pro-polypeptide region fused to the amino terminus of the fragment and/or an additional region fused to the carboxyl terminus of the fragment. However, several fragments may be comprised within a single larger polypeptide.

The polypeptides of the present invention or their immunogenic fragments (comprising at least one antigenic determinant) can be used to generate ligands, such as polyclonal or monoclonal antibodies, that are immunospecific for the polypeptides. Such antibodies may be employed to isolate or to identify clones expressing the polypeptides of the invention or to purify the polypeptides by affinity chromatography. The antibodies may also be employed as diagnostic or therapeutic aids, amongst other applications, as will be apparent to the skilled reader.

The term "immunospecific" means that the antibodies have substantially greater affinity for the polypeptides of the invention than their affinity for other related polypeptides in the prior art. As used herein, the term "antibody" refers to intact molecules as well as to fragments thereof, such as Fab, F(ab')2 and Fv, which are capable of binding to the antigenic determinant in question. Such antibodies thus bind to the polypeptides of the first aspect of the invention.

By "substantially greater affinity" we mean that there is a measurable increase in the affinity for a polypeptide of the invention as compared with the affinity for known secreted proteins.

Preferably, the affinity is at least 1.5-fold, 2-fold, 5-fold 10-fold, 100-fold, $10^3$-fold, $10^4$-fold, $10^5$-fold, $10^6$-fold or greater for a polypeptide of the invention than for known secreted proteins such as members of the IL-8 chemokine family of proteins.

If polyclonal antibodies are desired, a selected mammal, such as a mouse, rabbit, goat or horse, may be immunised with a polypeptide of the first aspect of the invention. The polypeptide used to immunise the animal can be derived by recombinant DNA technology or can be synthesized chemically. If desired, the polypeptide can be conjugated to a carrier protein. Commonly used carriers to which the polypeptides may be chemically coupled include bovine serum albumin, thyroglobulin and keyhole limpet haemocyanin. The coupled polypeptide is then used to immunise the animal. Serum from the immunised animal is collected and treated according to known procedures, for example by immunoaffinity chromatography.

Monoclonal antibodies to the polypeptides of the first aspect of the invention can also be readily produced by one skilled in the art. The general methodology for making monoclonal antibodies using hybridoma technology is well known (see, for example, Kohler, G. and Milstein, C., Nature 256: 495497 (1975); Kozbor et al., Immunology Today 4: 72 (1983); Cole et al., 77-96 in Monoclonal Antibodies and Cancer Therapy, Alan R. Liss, Inc. (1985).

Panels of monoclonal antibodies produced against the polypeptides of the first aspect of the invention can be screened for various properties, i.e., for isotype, epitope, affinity, etc. Monoclonal antibodies are particularly useful in purification of the individual polypeptide, against which they are directed. Alternatively, genes encoding the monoclonal antibodies of interest may be isolated from hybridomas, for instance by PCR techniques known in the art, and cloned and expressed in appropriate vectors.

Chimeric antibodies, in which non-human variable regions are joined or fused to human constant regions (see, for example, Liu et al., Proc. Natl. Acad. Sci. USA, 84, 3439 (1987)), may also be of use.

The antibody may be modified to make it less immunogenic in an individual, for example by humanisation (see Jones et al., Nature, 321, 522 (1986); Verhoeyen et al., Science, 239, 1534 (1988); Kabat et al., J. Immunol., 147, 1709 (1991); Queen et a., Proc. Natl Acad. Sci. USA, 86, 1029 (1989); Gorman et al., Proc. Natl Acad. Sci. USA, 88, 34181 (1991); and Hodgson et al., Bio/Technology, 9, 421 (1991)). The term "humanised antibody", as used herein, refers to antibody molecules in which the CDR amino acids and selected other amino acids in the variable domains of the heavy and/or light chains of a non-human donor antibody have been substituted in place of the equivalent amino acids in a human antibody. The humanised antibody thus closely resembles a human antibody but has the binding ability of the donor antibody.

In a further alternative, the antibody may be a "bispecific" antibody, that is an antibody having two different antigen binding domains, each domain being directed against a different epitope.

Phage display technology may be utilised to select genes which encode antibodies with binding activities towards the polypeptides of the invention either from repertoires of PCR amplified V-genes of lymphocytes from humans screened for possessing the relevant antibodies, or from naive libraries (McCafferty, J. et al, (11990), Nature 348, 552-554; Marks, J. et al., (1992) Biotechnology 10, 779-783). The affinity of these antibodies can also be improved by chain shuffling (Clackson, T. et al., (1991) Nature 352, 624-628).

Antibodies generated by the above techniques, whether polyclonal or monoclonal, have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme.

Preferred nucleic acid molecules of the second and third aspects of the invention are those which encode a polypeptide sequence as recited in SEQ ID NO:2, SEQ ID NO:4, SEQ ID NO:6, SEQ ID NO:8, SEQ ID NO:10 and SEQ ID NO:12 and functionally equivalent polypeptides. These nucleic acid molecules may be used in the methods and applications described herein. The nucleic acid molecules of the invention preferably comprise at least n consecutive nucleotides from the sequences disclosed herein where, depending on the particular sequence, n is 10 or more (for example, 12, 14, 15, 18, 20, 25, 30, 35, 40) or more).

The nucleic acid molecules of the invention also include sequences that are complementary to nucleic acid molecules described above (for example, for antisense or probing purposes).

Nucleic acid molecules of the present invention may be in the form of RNA, such as mRNA, or in the form of DNA, including, for instance cDNA, synthetic DNA or genomic DNA. Such nucleic acid molecules may be obtained by cloning, by chemical synthetic techniques or by a combination thereof. The nucleic acid molecules can be prepared, for example, by chemical synthesis using techniques such as solid phase phosphormidite chemical synthesis, from genomic or cDNA libraries or by separation from an organism. RNA molecules may generally be generated by the in vitro or in vivo transcription of DNA sequences.

The nucleic acid molecules may be double-stranded or single-stranded. Single-stranded DNA may be the coding strand, also known as the sense strand, or it may be the non-coding strand, also referred to as the anti-sense strand.

The term "nucleic acid molecule" also includes analogues of DNA and RNA, such a those containing modified backbones, and peptide nucleic acids (PNA). The term "PNA", as used herein, refers to an antisense molecule or an anti-gene agent which comprises an oligonucleotide of at least five nucleotides in length linked to a peptide backbone of amino acid residues, which preferably ends in lysine. The terminal lysine confers solubility to the composition. PNAs may be pegylated to extend their lifespan in a cell, where they preferentially bind complementary single stranded DNA and RNA and stop transcript elongation Nielsen, P. E. et al. (1993) Anticancer Drug Des. 8:53-63).

A nucleic acid molecule which encodes a polypeptide of this invention may be identical to the coding sequence of one or more of the nucleic acid molecules disclosed herein.

These molecules also may have a different sequence which, as a result of the degeneracy of the genetic code, encodes a polypeptide SEQ ID NO:2, SEQ ID NO:4, SEQ ID NO:6, SEQ ID NO:8, SEQ ID NO:10 or SEQ ID NO:12. Such nucleic acid molecules may include, but are not limited to, the coding sequence for the mature polypeptide by itself; the coding sequence for the mature polypeptide and additional coding sequences, such as those encoding a leader or secretory sequence, such as a pro-, pre- or prepro-polypeptide sequence; the coding sequence of the mature polypeptide, with or without the aforementioned additional coding sequences, together with further additional, non-coding sequences, including non-coding 5' and 3' sequences, such as the transcribed, non-translated sequences that play a role in transcription (including termination signals), ribosome binding and mRNA stability. The nucleic acid molecules may also include additional sequences which encode additional amino acids, such as those which provide additional functionalities.

The nucleic acid molecules of the second and third aspects of the invention may also encode the fragments or the functional equivalents of the polypeptides and fragments of the first aspect of the invention. Such a nucleic acid molecule may be a naturally-occurring variant such as a naturally-occurring allelic variant, or the molecule may be a variant that is not known to occur naturally. Such non-naturally occurring variants of the nucleic acid molecule may be made by mutagenesis techniques, including those applied to nucleic acid molecules, cells or organisms.

Among variants in this regard are variants that differ from the aforementioned nucleic acid molecules by nucleotide substitutions, deletions or insertions. The substitutions, deletions or insertions may involve one or more nucleotides. The variants may be altered in coding or non-coding regions or both. Alterations in the coding regions may produce conservative or non-conservative amino acid substitutions, deletions or insertions.

The nucleic acid molecules of the invention can also be engineered, using methods generally known in the art, for a variety of reasons, including modifying the cloning, processing, and/or expression of the gene product (the polypeptide). DNA shuffling by random fragmentation and PCR reassembly of gene fragments and synthetic oligonucleotides are included as techniques which may be used to engineer the nucleotide sequences. Site-directed mutagenesis may be used to insert new restriction sites, alter glycosylation patterns, change codon preference, produce splice variants, introduce mutations and so forth.

Nucleic acid molecules which encode a polypeptide of the first aspect of the invention may be ligated to a heterologous sequence so that the combined nucleic acid molecule encodes a fusion protein. Such combined nucleic acid molecules are included within the second or third aspects of the invention. For example, to screen peptide libraries for inhibitors of the activity of the polypeptide, it may be useful to express, using such a combined nucleic acid molecule, a fusion protein that can be recognised by a commercially-available antibody. A fusion protein may also be engineered to contain a cleavage site located between the sequence of the polypeptide of the invention and the sequence of a heterologous protein so that the polypeptide may be cleaved and purified away from the heterologous protein.

The nucleic acid molecules of the invention also include antisense molecules that are partially complementary to nucleic acid molecules encoding polypeptides of the present invention and that therefore hybridize to the encoding nucleic acid molecules (hybridization). Such antisense molecules, such as oligonucleotides, can be designed to recognise, specifically bind to and prevent transcription of a target nucleic acid encoding a polypeptide of the invention, as will be known by those of ordinary skill in the art (see, for example, Cohen, J. S., Trends in Pharm. Sci., 10, 435 (1989), Okano, J. Neurochem. 56, 560 (1991); O'Connor, J. Neurochem 56, 560 (1991); Lee et al., Nucleic Acids Res 6, 3073 (1979); Cooney et al., Science 241, 456 (1988); Dervan et al., Science 251, 1360 (1991).

The term "hybridization" as used here refers to the association of two nucleic acid molecules with one another by hydrogen bonding. Typically, one molecule will be fixed to a solid support and the other will be free in solution. Then, the two molecules may be placed in contact with one another under conditions that favour hydrogen bonding. Factors that affect this bonding include: the type and volume of solvent; reaction temperature; time of hybridization; agitation; agents to block the non-specific attachment of the liquid phase molecule to the solid support (Denhardt's reagent or BLOTTO); the concentration of the molecules; use of compounds to increase the rate of association of molecules (dextran sulphate or polyethylene glycol); and the stringency of the washing conditions following hybridization (see Sambrook et al. [supra]).

The inhibition of hybridization of a completely complementary molecule to a target molecule may be examined using a hybridization assay, as known in the art (see, for example, Sambrook et al. [supra]). A substantially homologous molecule will then compete for and inhibit the binding of a completely homologous molecule to the target molecule under various conditions of stringency, as taught in Wahl, G. M. and S. L. Berger (1987; Methods Enzymol. 152:399-407) and Kimmel, A. R. (1987; Methods Enzymol. 152:507-511).

"Stringency" refers to conditions in a hybridization reaction that favour the association of very similar molecules over association of molecules that differ. High stringency hybridisation conditions are defined as overnight incubation at 42° C. in a solution comprising 50% formamide, 5×SSC (150 mM ZaCl, 15 mM trisodiurm citrate), 50 mM sodium phosphate (pH7.6), 5× Denhardts solution, 10% dextran sulphate, and 20 microgram/ml denatured, sheared salmon sperm DNA, followed by washing the filters in 0.1×SSC at approximately 65° C. Low stringency conditions involve the hybridisation reaction being carried out at 35° C. (see Sambrook et al. [supra]). Preferably, the conditions used for hybridization are those of high stringency.

Preferred embodiments of this aspect of the invention are nucleic acid molecules that are at least 70% identical over their entire length to a nucleic acid molecule encoding the INSP085 polypeptides and nucleic acid molecules that are substantially complementary to such nucleic acid molecules. Preferably, a nucleic acid molecule according to this aspect of the invention comprises a region that is at least 80% identical over its enrtire length to such coding sequences, or is a nucleic acid molecule that is complementary thereto. In this regard, nucleic acid molecules at least 90%, preferably at least 95%, more preferably at least 98%, 99% or more identical over their entire length to the sanme are particularly preferred. Preferred embodiments in this respect are nucleic acid molecules that encode polypeptides which retain substantially the same biological function or activity as the INSP085 polypeptides.

The invention also provides a process for detecting a nucleic acid molecule of the invention, comprising the steps of: (a) contacting a nucleic probe according to the invention with a biological sample under hybridizing conditions to form duplexes; and (b) detecting any such duplexes that are formed.

As discussed additionally below in connection with assays that may be utilised according to the invention, a nucleic acid molecule as described above may be used as a hybridization probe for RNA, cDNA or genomic DNA, in order to isolate full-length cDNAs and genomic clones encoding the INSP085 polypeptides and to isolate cDNA and genomic clones of homologous or orthologous genes that have a high sequence similarity to the gene encoding this polypeptide.

In this regard, the following techniques, among others known in the art, may be utilised and are discussed below for purposes of illustration. Methods for DNA sequencing and analysis are well known and are generally available in the art and may, indeed, be used to practice many of "the embodiments of the invention discussed herein. Such methods may employ such enzymes as the Klenow fragment of DNA polymerase I, SEQUENASE™ (DNA sequencing kit) (U.S. BIOCHEMICAL CORP® Cleveland, OH), Taq polymerase (PERKIN ELMER®), thermostable T7 polymerase (AMERSHAM®, Chicago, IL), or combinations of polymerases and proof-reading exonucleases such as those found in the ELONGASE® (DNA polymerase mixture) Amplification System marketed by GIBCO/BRL® (Gaithersburg, MD). Preferably, the sequencing process may be automated using machines such as the Hamilton Micro Lab 2200 (Hamilton, Reno, NV), the Peltier Thermal Cycler (pTC200; MJ RESEARCH®, Watertown, MA) and the ABI Catalyst and 373 and 377 DNA Sequencers (PERKIN ELMER®).

One method for isolating a nucleic acid molecule encoding a polypeptide with an equivalent function to that of the INSP095 polypeptide is to probe a genomic or cDNA library with a natural or artificially-designed probe using standard procedures that are recognised in the art (see, for example, "Current Protocols in Molecular Biology", Ausubel et al. (eds). Greene Publishing Association and John Wiley Interscience, New York, 1989,1992). Probes comprising at least 15, preferably at least 30, and more preferably at least 50, contiguous bases that correspond to, or are complementary to, nucleic acid sequences from the appropriate encoding gene (SEQ ID NO:1, SEQ ID NO:3, SEQ ID NO:5, SEQ ID NO:7, SEQ ID NO:9 and SEQ ID NO:11), are particularly useful probes. Such probes may be labelled with an analytically-detectable reagent to facilitate their identification. Useful reagents include, but are not limited to, radioisotopes, fluorescent dyes and enzymes that are capable of catalysing the formation of a detectable product. Using these probes, the ordinarily skilled artisan will be capable of isolating complementary copies of genomic DNA, cDNA or RNA polynucleotides encoding proteins of interest from human, mammalian or other animal sources and screening such sources for related sequences, for example, for additional members of the family, type and/or subtype.

In many cases, isolated cDNA sequences will be incomplete, in that the region encoding the polypeptide will be cut short, normally at the 5' end. Several methods are available to obtain full length cDNAs, or to extend short cDNAs. Such sequences may be extended utilising a partial nucleotide sequence and employing various methods known in the art to detect upstream sequences such as promoters and regulatory elements. For example, one method which may be employed is based on the method of Rapid Amplification of cDNA Ends (RACE; see, for example, Frohman et al., PNAS USA 85, 8998-9002, 1988). Recent modifications of this technique, exemplified by the Marathon™ technology (CLONTECH® Laboratories Inc.), for example, have significantly simplified the search for longer cDNAs. A slightly different technique, termed "restriction-site" PCR, uses universal primers to retrieve unknown nucleic acid sequence adjacent a known locus (Sarkar, G. (1993) PCR Methods Applic. 2:318-322). Inverse PCR may also be used to amplify or to extend sequences using divergent primers based on a known region (Triglia, T. et al. (1988) Nucleic Acids Res. 16:8186). Another method which may be used is capture PCR which involves PCR amplification of DNA fragments adjacent a known sequence in human and yeast artificial chromosome DNA (Lagerstrom, M. et al. (1991) PCR Methods Applic. 1, 111-119). Another method which may be used to retrieve unknown sequences is that of Parker, J.D. et al. (1991); Nucleic Acids Res. 19:3055-3060). Additionally, one may use PCR, nested primers, and Promoter-Finder™ libraries to walk genomic DNA (CLONTECH®, Palo Alto, CA) This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences that contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

In one embodiment of the invention, the nucleic acid molecules of the present invention may be used for chromosome localisation. In this technique, a nucleic acid molecule is specifically targeted to, and can hybridize with, a particular location on an individual human chromosome. The mapping of relevant sequences to chromosomes according to the present invention is an important step in the confirmatory correlation of those sequences with the gene-associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationships between genes and diseases that have been mapped to the same chromosomal region are then identified through linkage analysis (coinheritance of physically adjacent genes). This provides valuable information to investigators searching for disease genes using positional cloning or other gene discovery techniques. Once the disease or syndrome has been crudely localised by genetic linkage to a particular genomic region, any sequences mapping to that area may represent associated or regulatory genes for further investigation. The nucleic acid molecule may also be used to detect differences in the chromosomal location due to translocation, inversion, etc. among normal, carrier, or affected individuals.

The nucleic acid molecules of the present invention are also valuable for tissue localisation. Such techniques allow the determination of expression patterns of the polypeptide in tissues by detection of the mRNAs that encode them. These techniques include in situ hybridization techniques and nucleotide amplification techniques, such as PCR. Results from these studies provide an indication of the normal functions of the polypeptide in the organism. In addition, comparative studies of the normal expression pattern of mRNAs with that of mRNAs encoded by a mutant gene provide valuable insights into the role of mutant polypeptides in disease. Such inappropriate expression may be of a temporal, spatial or quantitative nature.

Gene silencing approaches may also be undertaken to down-regulate endogenous expression of a gene encoding a polypeptide of the invention. RNA interference (RNAi) (Elbashir, S M et al., Nature 2001, 411, 494-498) is one method of sequence specific post-transcriptional gene silencing that may be employed. Short dsRNA oligonucleotides are synthesised in vitro and introduced into a cell. The sequence specific binding of these dsRNA oligonucleotides triggers the degradation of target mRNA, reducing or ablating target protein expression.

Efficacy of the gene silencing approaches assessed above may be assessed through the measurement of polypeptide expression (for example, by Western blotting), and at the RNA level using TaqMan-based methodologies.

The vectors of the present invention comprise nucleic acid molecules of the invention and may be cloning or expression vectors. The host cells of the invention, which may be transformed, transfected or transduced with the vectors of the invention may be prokaryotic or eukaryotic.

The polypeptides of the invention may be prepared in recombinant form by expression of their encoding nucleic acid molecules in vectors contained within a host cell. Such expression methods are well known to those of skill in the art and many are described in detail by Sambrook et al. (supra) and Fernandez & Hoeffler (1998, eds. "Gene expression systems Using nature for the art of expression". Academic Press, San Diego, London, Boston, New York, Sydney, Tokyo, Toronto).

Generally, any system or vector that is suitable to maintain, propagate or express nucleic acid molecules to produce a polypeptide in the required host may be used. The appropriate nucleotide sequence may be inserted into an expression system by any of a variety of well-known and routine techniques, such as, for example, those described in Sambrook et al., (supra). Generally, the encoding gene can be placed under the control of a control element such as a promoter, ribosome binding site (for bacterial expression) and, optionally, an operator, so that the DNA sequence encoding the desired polypeptide is transcribed into RNA in the transformed host cell.

Examples of suitable expression systems include, for example, chromosomal, episomal and virus-derived systems, including, for example, vectors derived from: bacterial plasmids, bacteriophage, transposons, yeast episomes, insertion elements, yeast chromosomal elements, viruses such as baculoviruses, papova viruses such as SV40, vaccinia viruses, adenoviuses, fowl pox viruses, pseudorabies viruses and retroviruses, or combinations thereof, such as those derived from plasmid and bacteriophage genetic elements, including cosmids and phagemids. Human artificial chromosomes (HACs) may also be employed to deliver larger fragments of DNA than can be contained and expressed in a plasmid.

Particularly suitable expression systems include microorganisms such as bacteria transformed with recombinant bacteriophage, plasmid or cosmid DNA expression vectors; yeast transformed with yeast expression vectors; insect cell systems infected with virus expression vectors (for example, baculovirus); plant cell systems transformed with virus expression vectors (for example, cauliflower mosaic virus, CaMV; tobacco mosaic virus, TMV) or with bacterial expression vectors (for example, Ti or pBR322 plasmids); or animal cell systems. Cell-free translation systems can also be employed to produce the polypeptides of the invention.

Introduction of nucleic acid molecules encoding a polypeptide of the present invention into host cells can be effected by methods described in many standard laboratory manuals, such as Davis et al., Basic Methods in Molecular Biology (1986) and Sambrook et al., (supra). Particularly suitable methods include calcium phosphate transfection, DEAE-dextran mediated transfection, transfection, microinjection, cationic lipid-mediated transfection, electroporation, transduction, scrape loading, ballistic introduction or infection (see Sambrook et al., 1989 [supra]; Ausubel et al., 1991 [supra]; Spector, Goldman & Leinwald, 1998). In eukaryotic cells, expression systems may either be transient (for example, episomal) or permanent (chromosomal integration) according to the needs of the system.

The encoding nucleic acid molecule may or may not include a sequence encoding a control sequence, such as a signal peptide or leader sequence, as desired, for example, for secretion of the translated polypeptide into the lumen of the endoplasmic reticulum, into the periplasmic space or into the extracellular environment. These signals may be endogenous to the polypeptide or they may be heterologous signals. Leader sequences can be removed by the bacterial host in post-translational processing.

In addition to control sequences, it may be desirable to add regulatory sequences that allow for regulation of the expression of the polypeptide relative to the growth of the host cell. Examples of regulatory sequences are those which cause the expression of a gene to be increased or decreased in response to a chemical or physical stimulus, including the presence of a regulatory compound or to various temperature or metabolic conditions.

Regulatory sequences are those non-translated regions of the vector, such as enhancers, promoters and 5' and 3' un-translated regions. These interact with host cellular proteins to carry out transcription and translation. Such regulatory sequences may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript phagemid (STRATAGENE®, LaJolla, CA) or pSport1™ plasmid (GIBCO/BRL®) and the like may be used. The baculovirus polyhedrin promoter may be used in insect cells. Promoters or enhancers derived from the genomes of plant cells (for example, heat shock, RUBISCO and storage protein genes) or from plant viruses (for example, viral promoters or leader sequences) may be cloned into the vector. In mammalian cell systems, promoters from mammalian genes or from mammalian viruses are preferable. If it is necessary to generate a cell line that contains multiple copies of the sequence, vectors based on SV40 or EBV may be used with an appropriate selectable marker.

An expression vector is constructed so that the particular nucleic acid coding sequence is located in the vector with the appropriate regulatory sequences, the positioning and orientation of the coding sequence with respect to the regulatory sequences being such that the coding sequence is transcribed under the "control" of the regulatory sequences, i.e., RNA polymerase which binds to the DNA molecule at the control sequences transcribes the coding sequence. In some cases it may be necessary to modify the sequence so that it may be attached to the control sequences with the appropriate orientation; i.e., to maintain the reading frame.

The control sequences and other regulatory sequences may be ligated to the nucleic acid coding sequence prior to insertion into a vector. Alternatively, the coding sequence can be cloned directly into an expression vector that already contains the control sequences and an appropriate restriction site.

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BEK), monkey kidney (COS), C127, 3T3, BHK, HEK 293, Bowes melanoma and human hepatocelluar carcinoma (for example Hep G2) cells and a number of other cell lines.

In the baculovirus system, the materials for baculovirus/insect cell expression systems are commercially available in kit form from, inter alia, INVITROGEN®, San Diego CA (the "MaxBac" kit). These techniques are generally known to those skilled in the art and are described fully in Summers and Smith, Texas Agricultural Experiment Station Bulletin No. 1555 (1987). Particularly suitable host cells for use in this system include insect cells such as Drosophila 82 and Spodoptera Sf9 cells.

There are many plant cell culture and whole plant genetic expression systems known in the art. Examples of suitable plant cellular genetic expression systems include those described in U.S. Pat. No. 5,693,506; U.S. Pat. No. 5,659,122; and U.S. Pat. No. 5,608,143. Additional examples of genetic expression in plant cell culture has been described by Zenk, Phytochemistry 30, 3861-3863 (1991).

In particular, all plants from which protoplasts can be isolated and cultured to give whole regenerated plants can be utilised, so that whole plants are recovered which contain the transferred gene. Practically all plants cam be regenerated from cultured cells or tissues, including but not limited to all major species of sugar cane, sugar beet, cotton, fruit and other trees, legumes and vegetables.

Examples of particularly preferred bacterial host cells include *streptococci, staphylococci, E. coli, Streptomyces* and *Bacillus subtilis* cells.

Examples of particularly suitable host cells for fungal expression include yeast cells (for example, *S. cerevisiae*) and *Aspergillus* cells.

Any number of selection systems are known in the art that may be used to recover transformed cell lines. Examples include the herpes simplex virus thymidine kinase (Wigler, M. et al. (1977) Cell 11:223-32) and adenine phosphoribosyltransferase (Lowy, I. et al. (1980) Cell 22:817-23) genes that can be employed in tk⁻ or aprt± cells, respectively.

Also, antimetabolite, antibiotic or herbicide resistance can be used as the basis for selection; for example, dihydrofolate reductase (DHFR) that confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al. (1981) J. Mol. Biol. 150:1-14) and als or pat, which confer resistance to chlorsulfuron and phosphinotricin acetyltransferase, respectively. Additional selectable genes have been described, examples of which will be clear to those of skill in the art.

Although the presence or absence of marker gene expression suggests that the gene of interest is also present, its presence and expression may need to be confirmed. For example, if the relevant sequence is inserted within a marker gene sequence, transformed cells containing the appropriate sequences can be identified by the absence of marker gene function. Alternatively, a marker gene can be placed in tandem with a sequence encoding a polypeptide of the invention under the control of a single promoter. Expression of be marker gene in response to induction or selection usually indicates expression of the tandem gene as well.

Alternatively, host cells that contain a nucleic acid sequence encoding a polypeptide of the invention and which express said polypeptide may be identified by a variety of procedures known to those of skill in the art. These procedures include, but are not limited to, DNA-DNA or DNA-RNA hybridizations and protein bioassays, for example, fluorescence activated cell sorting (FACS) or immunoassay techniques (such as the enzyme-linked immunosorbent assay [ELISA] and radioimmunoassay [RIA]), that include membrane, solution, or chip based technologies for the detection and/or quantification of nucleic acid or protein (see Hampton, R. et al. (1990) Serological Methods, a Laboratory Manual, APS Press, St Paul, Minn.) and Maddox, D. E. et al. (1983) J. Exp. Med, 158, 1211-1216).

A wide variety of labels and conjugation techniques are known by those skilled in the art and may be used in various nucleic acid and amino acid assays. Means for producing labelled hybridization or PCR probes for detecting sequences related to nucleic acid molecules encoding polypeptides of the present invention include oligolabelling, nick translation, end-labelling or PCR amplification using a labelled polynucleotide. Alternatively, the sequences encoding the polypeptide of the invention may be cloned into a vector for the production of an mRNA probe. Such vectors are known in the art, are commercially available, and may be used to synthesise RNA probes in vitro by addition of an appropriate RNA polinerase such as T7, T3 or SP6 and labelled nucleotides. These procedures may be conducted using a variety of commercially available kits (PHARMACIA & UPJOHN®, (Kalamazoo, MD); PROMEGA (Madison WI); and U.S. Biochemical Corp., Cleveland, OH)).

Suitable reporter molecules or labels, which may be used for ease of detection, include radionuclides, enzymes and fluorescent, chemiluminescent or chromogenic agents as well as substrates, cofactors, inhibitors, magnetic particles, and the like.

Nucleic acid molecules according to the present invention may also be used to create transgenic animals, particularly rodent animals. Such transgenic animals form a further aspect of the present invention. This may be done locally by modification of somatic cells, or by germ line therapy to incorporate heritable modifications. Such transgenic animals may be particularly useful in the generation of animal models for drug molecules effective as modulators of the polypeptides of the present invention.

The polypeptide can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography is particularly useful for purification. Well known techniques for refolding proteins may be employed to regenerate an active conformation when the polypeptide is denatured during isolation and or purification.

Specialised vector constructions may also be used to facilitate purification of proteins, as desired, by joining sequences encoding the polypeptides of the invention to a nucleotide sequence encoding a polypeptide domain that will facilitate purification of soluble proteins. Examples of such purification-facilitating domains include metal chelating peptides such as histidine-tryptophan modules that allow purification on immobilised metals, protein A domains that allow purification on immobilised immunoglobulin, and the domain utilised in the FLAGS extension/affinity purification system (IMMUNEX® Corp., Seattle, WA). The inclusion of cleavable linker sequences such as those specific for Factor XA or enterokinase (INVITROGEN®, San. Diego, CA) between the purification domain and the polypeptide of the invention may be used to facilitate purification. One such expression vector provides for expression of a fusion protein containing the polypeptide of the invention fused to several histidine residues preceding a thioredoxin or an enterokinase cleavage site. The histidine residues facilitate purification by IMAC (immobilised metal ion affinity chromatography as described in Porath, J. et al. (1992), Prot. Exp. Purif. 3: 263-281) while the thioredoxin or enterokinase cleavage site provides a means for purifying the polypeptide from the fusion protein. A discussion of vectors which contain fusion proteins is provided in Kroll, D.J. et al. (1993; DNA Cell Biol. 12:441-453).

If the polypeptide is to be expressed for use in screening assays, generally it is preferred that it be produced at the surface of the host cell in which it is expressed. In this event, the host cells may be harvested prior to use in the screening assay, for example using techniques such as fluorescence activated cell sorting (FACS) or immunoaffinity techniques. If the polypeptide is secreted into the medium, the medium can be recovered in order to recover and purify the expressed polypeptide. If polypeptide is produced intracellularly, the cells must first be lysed before the polypeptide is recovered.

The polypeptide of the invention can be used to screen libraries of compounds in any of a variety of drug screening techniques. Such compounds may activate (agonise) or inhibit (antagonise) the level of expression of the gene or the activity of the polypeptide of the invention and form a further aspect of the present invention. Preferred compounds are effective to alter the expression of a natural gene which encodes a polypeptide of the first aspect of the invention or to regulate the activity of a polypeptide of the first aspect of the invention.

Agonist or antagonist compounds may be isolated from, for example, cells, cell-free preparations, chemical libraries or natural product mixtures. These agonists or antagonists may be natural or modified substrates, ligands, enzymes, receptors or structural or functional mimetics. For a suitable review of such screening techniques, see Coligan et al., Current Protocols in Immunology 1(2):Chapter 5 (1991).

Compounds that are most likely to be good antagonists are molecules that bind to the polypeptide of the invention without inducing the biological effects of the polypeptide upon binding to it. Potential antagonists include small organic molecules, peptides, polypeptides and antibodies that bind to the polypeptide of the invention and thereby inhibit or extinguish its activity. In this fashion, binding of the polypeptide to normal cellular binding molecules may be inhibited, such that the normal biological activity of the polypeptide is prevented.

The polypeptide of the invention that is employed in such a screening technique may be free in solution, affixed to a solid support, borne on a cell surface or located intracellularly. In general, such screening procedures may involve using appropriate cells or cell membranes that express the polypeptide that are contacted with a test compound to observe binding, or stimulation or inhibition of a functional response. The functional response of the cells contacted with the test compound is then compared with control cells that were not contacted with the test compound. Such an assay may assess whether the test compound results in a signal generated by activation of the polypeptide, using an appropriate detection system. Inhibitors of activation are generally assayed in the presence of a known agonist and the effect on activation by the agonist in the presence of the test compound is observed.

A preferred method for identifying an agonist or antagonist compound of a polypeptide of the present invention comprises:

(a) contacting a cell expressing or the surface thereof the polypeptide according to the first aspect of the invention, the polypeptide being associated with a second component capable of providing a detectable signal in response to the binding of a compound to the polypeptide, with a compound to be screened under conditions to permit binding to the polypeptide; and (b) determining whether the compound binds to and activates or inhibits the polypeptide by measuring the level of a signal generated from the interaction of the compound with the polypeptide.

A further preferred method for identifying an agonist or antagonist of a polypeptide of the invention comprises:

(a) contacting a cell expressing on the surface thereof the polypeptide, the polypeptide being associated with a second component capable of providing a detectable signal in response to the binding of a compound to the polypeptide, with a compound to be screened under conditions to permit binding to the polypeptide; and (b) determining whether the compound binds to and activates or inhibits the polypeptide by comparing the level of a signal generated from the interaction of the compound with the polypeptide with the level of a signal in the absence of the compound.

In further preferred embodiments, the general methods that are described above may further comprise conducting the identification of agonist or antagonist in the presence of labelled or unlabelled ligand for the polypeptide.

In another embodiment of the method for identifying an agonist or antagonist of a polypeptide of the present invention comprises:

determining the inhibition of binding of a ligand to cells which have a polypeptide of the invention on the surface thereof, or to cell membranes containing such a polypeptide, in the presence of a candidate compound under conditions to permit binding to the polypeptide, and determining the amount of ligand bound to the polypeptide. A compound capable of causing reduction of binding of a ligand is considered to be an agonist or antagonist. Preferably the ligand is labelled.

More particularly, a method of screening for a polypeptide antagonist or agonist compound comprises the steps of:

(a) incubating a labelled ligand with a whole cell expressing a polypeptide according to the invention on the cell surface, or a cell membrane containing a polypeptide of the invention, (b) measuring the amount of labelled ligand bound to the whole cell or the cell membrane;

(c) adding a candidate compound to a mixture of labelled ligand and the whole cell or the cell membrane of step (a) and allowing the mixture to attain equilibrium;

(d) measuring the amount of labelled ligand bound to the whole cell or the cell membrane after step (c); and (e) comparing the difference in the labelled ligand bound in step (b) and (d), such that the compound which causes the reduction in binding in step (d) is considered to be an agonist or antagonist.

The INSP085 polypeptides may also be found to modulate immune and/or nervous system cell proliferation and differentiation in a dose-dependent manner in the above-described assays. Thus, the "functional equivalents" of the INSP085 polypeptides include polypeptides that exhibit any of the same growth and differentiation regulating activities in the above-described assays in a dose-dependent manner. Although the degree of dose-dependent activity need not be identical to that of the INSP085 polypeptides, preferably the "functional equivalents" will exhibit substantially similar dose-dependence in a given activity assay compared to the INSP085 polypeptides.

In certain of the embodiments described above, simple binding assays may be used, in which the adherence of a test compound to a surface bearing the polypeptide is detected by means of a label directly or indirectly associated with the test compound or in an assay involving competition with a labelled competitor. In another embodiment, competitive drug screening assays may be used, in which neutralising antibodies that are capable of binding the polypeptide specifically compete with a test compound for binding. In this manner, the antibodies can be used to detect the presence of any test compound that possesses specific binding affinity for the polypeptide.

Assays may also be designed to detect the effect of added test compounds on the production of mRNA encoding the polypeptide in cells. For example, an ELISA may be constructed that measures secreted or cell-associated levels of polypeptide using monoclonal or polyclonal antibodies by standard methods known in the art, and this can be used to search for compounds that may inhibit or enhance the production of the polypeptide from suitably manipulated cells or tissues. The formation of binding complexes between the polypeptide and the compound being tested may then be measured.

Another technique for drug screening which may be used provides for high throughput screening of compounds having suitable binding affinity to the polypeptide of interest (see International patent application WO84/03564). In this method, large numbers of different small test compounds are synthesised on a solid substrate, which may then be reacted with the polypeptide of the invention and washed. One way of immobilising the polypeptide is to use non-neutralising antibodies. Bound polypeptide may then be detected using methods that are well known in the art. Purified polypeptide can also be coated directly onto plates for use in the aforementioned drug screening techniques.

The polypeptide of the invention may be used to identify membrane-bound or soluble receptors, through standard receptor binding techniques that are known in the art, such as ligand binding and crosslinking assays in which the polypeptide is labelled with a radioactive isotope, is chemically modified, or is fused to a peptide sequence that facilitates its detection or purification, and incubated with a source of the putative receptor (for example, a composition of cells, cell membranes, cell supernatants, tissue extracts, or bodily fluids). The efficacy of binding may be measured using biophysical techniques such as surface plasmon resonance and spectroscopy. Binding assays may be used for the purification and cloning of the receptor, but may also identify agonists and antagonists of the polypeptide, that compete with the binding of the polypeptide to its receptor. Standard methods for conducting screening assays are well understood in the art.

The invention also includes a screening kit useful in the methods for identifying agonists, antagonists, ligands, receptors, substrates, enzymes, that are described above.

The invention includes the agonists, antagonists, ligands, receptors, substrates and enzymes, and other compounds which modulate the activity or antigenicity of the polypeptide of the invention discovered by the methods that are described above.

The invention also provides pharmaceutical compositions comprising a polypeptide, nucleic acid, ligand or compound of the invention in combination with a suitable pharmaceutical carrier. These compositions may be suitable as therapeutic or diagnostic reagents, as vaccines, or as other immunogenic compositions, as outlined in detail below.

According to the terminology used herein, a composition containing a polypeptide, nucleic acid, ligand or compound [X] is "substantially free of" impurities [herein, Y] when at least 85% by weight of the total X+Y in the composition is X. Preferable, X comprises at least about 90% by weight of the total of X+Y in the composition, more preferably at least about 95%, 98% or even 99% by weight.

The pharmaceutical compositions should preferably comprise a therapeutically effective amount of the polypeptide, nucleic acid molecule, ligand, or compound of the invention. The term "therapeutically effective amount" as used herein refers to an amount of a therapeutic agent needed to treat, ameliorate, or prevent a targeted disease or condition, or to exhibit a detectable therapeutic or preventative effect. For any compound, the therapeutically effective dose can be estimated initially either in cell culture assays, for example, of neoplastic cells, or in animal models, usually mice, rabbits, dogs, or pigs. The animal model may also be used to determine the appropriate concentration range and route of administration. Such information can then be used to determine useful doses and routes for administration in humans.

The precise effective amount for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. Generally, an effective dose will be from 0.01 mg/kg to 50 mg/kg, preferably 0.05 mg/kg to 10 mg/kg Compositions may be administered individually to a patient or may be administered in combination with other agents, drugs or hormones.

A pharmaceutical composition may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity. Suitable carriers may be large, slowly metabolised macromolecules such as proteins, polysaccharides, polylactic acids, polyglycolic acids, polymeric amino acids, amino acid copolymers and inactive virus particles.

Pharmaceutically acceptable salts can be used therein, for example, mineral acid salts such as hydrochlorides, hydrobromides, phosphates, sulphates, and the like; and the salts of organic acids such as acetates, propionates, malonates, benzoates, and the like. A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated cars be animals; in particular, human subjects can be treated.

The pharmaceutical compositions utilised in this invention may be administered by any number of routes including, but not limited to, oral, intravenous, intramuscular, intraarterial, intramedullary, intrathecal, intraventricular, transdermal or transcutaneous applications (for example, see WO98/20734), subcutaneous, intraperitoneal, intranasal, enteral, topical, sublingual, intravaginal or rectal means. Gene guns or hyposprays may also be used to administer the pharmaceutical compositions of the invention. Typically, the therapeutic compositions may be prepared as injectables, either as liquid solutions or suspensions; solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

If the activity of the polypeptide of the invention is in excess in a particular disease state, several approaches are available. One approach comprises administering to a subject an inhibitor compound (antagonist) as described above, along with a pharmaceutically acceptable carrier in an amount effective to inhibit the function of the polypeptide, such as by blocking the binding of ligands, substrates, enzymes, receptors, or by inhibiting a second signal, and thereby alleviating the abnormal condition. Preferably, such antagonists are antibodies. Most preferably, such antibodies are chimeric and/or humanised to minimise their immunogenicity, as described previously.

In another approach, soluble forms of the polypeptide that retain binding affinity for the ligand, substrate, enzyme, receptor, in question, may be administered. Typically, the polypeptide may be administered in the form of fragments that retain the relevant portions.

In an alternative approach, expression of the gene encoding the polypeptide can be inhibited using expression blocking techniques, such as the use of antisense nucleic acid molecules (as described above), either internally generated or separately administered. Modifications of gene expression can be obtained by designing complementary sequences or antisense molecules (DNA, RNA, or PNA) to the control, 5' or regulatory regions (signal sequence, promoters, enhancers and introns) of the gene encoding the polypeptide. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, Molecular and Immunologic Approaches, Futura Publishing Co., Mt. Kisco, N.Y.). The complementary sequence or antisense molecule may also be designed to block translation of mRNA by preventing the transcript from binding to ribosomes. Such oligonucleotides may be administered or may be generated in situ from expression in vivo.

In addition, expression of the polypeptide of the invention may be prevented by using ribozymes specific to its encoding mRNA sequence. Ribozymes are catalytically active RNAs that can be natural or synthetic (see for example Usman, N, et al., Curr. Opin. Struct. Biol (1996) 6(4), 527-33). Synthetic ribozymes can be designed to specifically cleave mRNAs at selected positions thereby preventing translation of the mRNAs into functional polypeptide. Ribozymes may be synthesised with a natural ribose phosphate backbone and natural bases, as normally found in RNA molecules. Alternatively the ribozymes may be synthesised with non-natural backbones, for example, 2'-O-methyl RNA, to provide protection from ribonuclease degradation and may contain modified bases.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of non-traditional bases such as inosine, queosine and butosine, as well as acetyl-, methyl-, thio- and similarly modified forms of adenine, cytidine, guanine, thymine ad uridine which are not as easily recognised by endogenous endonucleases.

For treating abnormal conditions related to an underexpression of the polypeptide of the invention and its activity, several approaches are also available. One approach comprises administering to a subject a therapeutically effective amount of a compound that activates the polypeptide, i.e., an agonist as described above, to alleviate the abnormal condition. Alternatively, a therapeutic amount of the polypeptide in combination with a suitable pharmaceutical carrier may be administered to restore the relevant physiological balance of polypeptide.

Gene therapy may be employed to effect the endogenous production of the polypeptide by the relevant cells in the subject. Gene therapy is used to treat permanently the inappropriate production of the polypeptide by replacing a defective gene with a corrected therapeutic gene.

Gene therapy of the present invention can occur ire vivo or ex vivo. Ex vivo gene therapy requires the isolation and purification of patient cells, the introduction of a therapeutic gene and introduction of the genetically altered cells back into the patient. In contrast, in vivo gene therapy does not require isolation and purification of a patient's cells.

The therapeutic gene is typically "packaged" for administration to a patient. Gene delivery vehicles may be non-viral, such as liposomes, or replication-deficient viruses, such as adenovirus as described by Berkner, K.L., in Curr. Top. Microbiol. Immnunol., 158, 39-66 (1992) or adeno-associated virus (AAV) vectors as described by Muzyczka, N., in Curr. Top. Microbiol. Immunol., 158, 97-129 (1992) and U.S. Pat. No. 5,252,479. For example, a nucleic acid molecule encoding a polypeptide of the invention may be engineered for expression in a replication-defective retroviral vector. This expression construct may then be isolated and introduced into a packaging cell transduced with a retroviral plasmid vector containing RNA encoding the polypeptide, such that the packaging cell now produces infectious viral particles containing the gene of interest. These producer cells may be administered to a subject for engineering cells in vivo and expression of the polypeptide in vivo (see Chapter 20, Gene Therapy and other Molecular Genetic-based Therapeutic Approaches, (and references cited therein) in Human Molecular Genetics (1996), T Strachan and A P Read, BIOS Scientific Publishers Ltd).

Another approach is the adminstration of "naked DNA" in which the therapeutic gene is directly injected into the bloodstream or muscle tissue.

In situations in which the polypeptides or nucleic acid molecules of the invention are disease-causing agents, the invention provides that they can be used in vaccines to raise antibodies against the disease causing agent.

Vaccines according to the invention may either be prophylactic (i.e. to prevent infection) or therapeutic (i.e. to treat disease after infection). Such vaccines comprise immunising antigen(s), immunogen(s), polypeptide(s), protein(s) or nucleic acid, usually in combination with pharmaceutically-acceptable carriers as described above, which include any carrier that does not itself induce the production of antibodies harmful to the individual receiving the composition. Additionally, these carriers may function as immuno-stimulating agents ("adjuvants"). Furthermore, the antigen or immunogen may be conjugated to a bacterial toxoid, such as a toxoid from diphtheria, tetanus, cholera, *H. pylori*, and other pathogens.

Since polypeptides may be broken down in the stomach, vaccines comprising polypeptides are preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation isotonic with the blood of the recipient, and aqueous and non-aqueous sterile suspensions which may include suspending agents or thickening agents.

The vaccine formulations of the invention may be presented in unit-dose or multi-dose containers. For example, sealed ampoules and vials and may be stored in a freeze-dried condition requiring only the addition of the sterile liquid carrier immediately prior to use. The dosage will depend on the specific activity of the vaccine and can be readily determined by routine experimentation.

Genetic delivery of antibodies that bind to polypeptides according to the invention may also be effected, for example, as described in International patent application WO98/55607.

The technology referred to as jet injection (see, for example, www.powderject.com) may also be useful in the formulation of vaccine compositions.

A number of suitable methods for vaccination and vaccine delivery systems are described in International patent application WO00/29428.

This invention also relates to the use of nucleic acid molecules according to the present invention as diagnostic reagents. Detection of a mutated form of the gene characterised by the nucleic acid molecules of the invention which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acid molecules for diagnosis may be obtained from a subject's cells, such as from blood, urine, saliva, tissue biopsy or autopsy material. The genomic DNA may be used directly for detection or may be amplified emzymatically by using PCR, ligase chain reaction (LCR), strand displacement amplification (SDA), or other amplification techniques (see Saiki et al., Nature, 324, 163-166 (1986); Bej, et al., Crit. Rev. Biochem. Molec. Biol., 26, 301-334 (1991); Birkenmeyer et al., J. Virol. Meth., 35, 117-126 (1991); Van Brunt, J., Bio/Technology, 8,291-294 (1990)) prior to analysis.

In one embodiment, this aspect of the invention provides a method of diagnosing a disease in a patient, comprising assessing the level of expression of a natural gene encoding a polypeptide according to the invention and comparing said level of expression to a control level, wherein a level that is different to said control level is indicative of disease. The method may comprise the steps of:

a) contacting a sample of tissue from the patient with a nucleic acid probe under stringent conditions that allow the formation of a hybrid complex between a nucleic acid molecule of the invention and the probe;

b) contacting a control sample with said probe under the same conditions used in step a);

c) and detecting the presence of hybrid complexes in said samples;

wherein detection of levels of the hybrid complex in the patient sample that differ from levels of the hybrid complex in the control sample is indicative of disease.

A further aspect of the invention comprises a diagnostic method comprising the steps of:

a) obtaining a tissue sample from a patient being tested for disease;

b) isolating a nucleic acid molecule according to the invention from said tissue sample; and c) diagnosing the patient for disease by detecting the presence of a mutation in the nucleic acid molecule which is associated with disease.

To aid the detection of nucleic acid molecules in the above-described methods, an amplification step, for example using PCR, may be included.

Deletions and insertions can be detected by a change in the size of the amplified product in comparison to the normal genotype. Point mutations can be identified by hybridizing amplified DNA to labelled RNA of the invention or alternatively, labelled antisense DNA sequences of the invention. Perfectly-matched sequences can be distinguished from mismatched duplexes by RNase digestion or by assessing differences in melting temperatures. The presence or absence of the mutation in the patient may be detected by contacting DNA with a nucleic acid probe that hybridises to the DNA under stringent conditions to form a hybrid double-stranded molecule, the hybrid double-stranded molecule having an unhybridised portion of the nucleic acid probe strand at any portion corresponding to a mutation associated with disease; and detecting the presence or absence of an unhybridised portion of the probe strand as an indication of the presence or absence of a disease-associated mutation in the corresponding portion of the DNA strand.

Such diagnostics are particularly useful for prenatal and even neonatal testing.

Point mutations and other sequence differences between the reference gene and "mutant" genes can be identified by other well-known techniques, such as direct DNA sequencing or single-strand conformational polymorphism, (see Orita et al., Genomics, 5, 874-879 (1989)). For example, a sequencing primer may be used with double-stranded PCR product or a single-stranded template molecule generated by a modified PCR. The sequence determination is performed by conventional procedures with radiolabelled nucleotides or by automatic sequencing procedures with fluorescent-tags. Cloned DNA segments may also be used as probes to detect specific DNA segments. The sensitivity of this method is greatly enhanced when combined with PCR. Further, point mutations and other sequence variations, such as polymorphisms, can be detected as described above, for example, through the use of allele-specific oligonucleotides for PCR amplification of sequences that differ by single nucleotides.

DNA sequence differences may also be detected by alterations in the electrophoretic mobility of DNA fragments in gels, with or without denaturing agents, or by direct DNA sequencing (for example, Myers et al., Science (1985) 230:1242) Sequence changes at specific locations may also be revealed by nuclease protection assays, such as RNase and S1 protection or the chemical cleavage method (see Cotton et al., Proc. Natl. Acad. Sci. USA (1985) 85: 4397-4401).

In addition to conventional gel electrophoresis and DNA sequencing, mutations such as microdeletions, aneuploidies, translocations, inversions, can also be detected by in situ analysis (see, for example, Keller et al., DNA Probes, 2nd Ed., Stockton Press, New York, N.Y., USA (1993)), that is, DNA or RNA sequences in cells can be analysed for mutations without need for their isolation and/or immobilisation onto a membrane. Fluorescence in situ hybridization (FISH) is presently the most commonly applied method and numerous reviews of FISH have appeared (see, for example, Trachuck et al., Science, 250, 559-562 (1990), and Trask et al., Trends, Genet, 7, 149-154 (1991)).

In another embodiment of the invention, an array of oligonucleotide probes comprising a nucleic acid molecule according to the invention can be constructed to conduct efficient screening of genetic variants, mutations and polymorphisms. Array technology methods are well known and have general applicability and can be used to address a variety of questions in molecular genetics including gene expression, genetic linkage, and genetic variability (see for example: M. Chee et al., Science (1996), Vol 274, pp 610-613).

In one embodiment, the array is prepared and used according to the methods described in PCT application WO95/11995 (Chee et al); Lockhart, D. J. et al. (1996) Nat. Biotech. L4: 1675-1680); and Schena, M. et al. (1996) Proc. Natl. Acad. Sci. 93: 10614-10619). Oligonucleotide pairs may range from two to over one million. The oligomers are synthesized at designated areas on a substrate using a light-directed chemical process. The substrate may be paper, nylon or other type of membrane, filter, chip, glass slide or any other suitable solid support. In another aspect, an oligonucleotide may be synthesized on the surface of the substrate by using a chemical coupling procedure and an ink jet application apparatus, as described ii PCT application WO95/25116 (Baldeschweiler et al.). In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and over one million which lends itself to the efficient use of commercially-available instrumentation.

In addition to the methods discussed above, diseases may be diagnosed by methods comprising determining, from a sample derived from a subject, an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods.

Assay techniques that can be used to determine levels of a polypeptide of the present invention in a sample derived from a host are well-known to those of skill in the art and are discussed in some detail above (including radioimmunoassays, competitive-binding assays, Western Blot analysis ad ELISA assays). This aspect of the invention provides a diagnostic method which comprises the steps of: (a) contacting a ligand as described above with a biological sample under conditions suitable for the formation of a ligand-polypeptide complex; and (b) detecting said complex.

Protocols such as ELISA, RIA, and FACS for measuring polypeptide levels may additionally provide a basis for diagnosing altered or abnormal levels of polypeptide expression. Normal or standard values for polypeptide expression are established by combining body fluids or cell extracts taken from normal mammalian subjects, preferably humans, with antibody to the polypeptide under conditions suitable for complex formation The amount of standard complex formation may be quantified by various methods, such as by photometric means.

Antibodies which specifically bind to a polypeptide of the invention may be used for the diagnosis of conditions or diseases characterised by expression of the polypeptide, or in assays to monitor patients being treated with the polypeptides, nucleic acid molecules, ligands and other compounds of the invention. Antibodies useful for diagnostic purposes may be prepared in the same manner as those described above for therapeutics. Diagnostic assays for the polypeptide include methods that utilise the antibody and a label to detect the polypeptide in human body fluids or extracts of cells or tissues. The antibodies may be used with or without modification, and may be labelled by joining them, either covalently or non-covalently, with a reporter molecule. A wide variety of reporter molecules known in the art may be used, several of which are described above.

Quantities of polypeptide expressed in subject, control and disease samples from biopsied tissues are compared with the standard values. Deviation between standard and subject values establishes the parameters for diagnosing disease. Diagnostic assays may be used to distinguish between absence, presence, and excess expression of polypeptide and to monitor regulation of polypeptide levels during therapeutic intervention. Such assays may also be used to evaluate the efficacy of a particular therapeutic treatment regimen in animal studies, in clinical trials or in monitoring the treatment of an individual patient.

A diagnostic kit of the present invention may comprise:
(a) a nucleic acid molecule of the present invention;
(b) a polypeptide of the present invention; or
(c) a ligand of the present invention.

In one aspect of the invention, a diagnostic kit may comprise a first container containing a nucleic acid probe that hybridises under stringent conditions with a nucleic acid molecule according to the invention; a second container containing primers useful for ampling the nucleic acid molecule; and instructions for using the probe and primers for facilitating the diagnosis of disease. The kit may further comprise a third container holding an agent for digesting unhybridised RNA.

In an alternative aspect of the invention, a diagnostic kit may comprise an array of nucleic acid molecules, at least one of which may be a nucleic acid molecule according to the invention.

To detect polypeptide according to the invention, a diagnostic kit may comprise one or more antibodies that bind to a polypeptide according to the invention; and a reagent useful for the detection of a binding reaction between the antibody and the polypeptide.

Such kits will be of use in diagnosing a disease or susceptibility to disease in which members of the IL-8 like chemokine family are implicated. Such diseases may include cell proliferative disorders, including neoplasm, melanoma, lung, colorectal, breast, pancreas, head and neck and other solid tumours; myeloproliferative disorders, such as leukemia, non-Hodgkin lymphoma, leukopenia, thrombocytopenia, angiogenesis disorder, Kaposis' sarcoma; autoimmune/inflammatory disorders, including allergy, inflammatory bowel disease, arthritis, psoriasis and respiratory tract inflammation, asthma, and organ transplant rejection; cardiovascular disorders, including hypertension, oedema, angina, atherosclerosis, thrombosis, sepsis, shock, reperfusion injury, and ischemia; neurological disorders including central nervous system disease, Alzheimer's disease, brain injury, amyotrophic lateral sclerosis, and pain; developmental disorders; metabolic disorders including diabetes mellitus, osteoporosis, and obesity, AIDS and renal disease; infections including viral infection, bacterial infection, fungal infection and parasitic infection and other pathological conditions. Preferably, the diseases are those in which members of the IL-8 like chemokine family are implicated such as arthritis, rheumatoid arthritis (RA), psoriatic arthritis, osteoarthritis, systemic lupus erythematosus (SLE), systemic sclerosis, scleroderma, polymyositis, glomerulonephritis, fibrosis, lung fibrosis and inflammation, allergic or hypersensitvity diseases, dermatitis, asthma, chronic obstructive pulmonary disease (COPD), inflammatory bowel disease (IBD), Crohn's diseases, ulcerative colitis, multiple sclerosis, septic shock, HIV infection, transplant rejection, wound healing, metastasis, endometriosis, hepatitis, lived fibrosis, cancer, analgesia, and vascular inflammation related to atherosclerosis. Such kits may also be used for the detection of reproductive disorders including infertility.

Various aspects and embodiments of the present invention will now be described in more detail by way of example, with particular reference to the INSP085 polypeptides.

It will be appreciated that modification of detail may be made with-out departing from the scope of the invention.

BRIEF DESCRIPTION OF THE FIGURES

FIG. 1: Top ten results from BLAST against NCBI non-redundant database using SEQ ID NO:8 (INSP085 full protein sequence).

FIG. 2: Alignment generated by BLAST between SEQ ID NO:8 (INSP085 full protein sequence) and the top five hits, small inducible cytokine subfamily B member 15 (*Mus musculus*), K60 protein (*Gallus gallus*), sheep IL-8 precursor (*Ovis aries*), pig IL-8 precursor (*Sus scrofa*) and bovine IL-8 precursor (*Bos taurus*).

FIG. 3: Sig P cleavage site prediction for INSP085.

FIG. 4: Sig P peptide prediction for INSP085.

FIG. 5: INSP085 coding exon organisation in genomic DNA and position of PCR primers.

FIG. 6: Nucleotide sequence and translation of cloned INSP085 ORF

EXAMPLES

Example 1

INSP085 Protein BLAST Results

Figure 7:
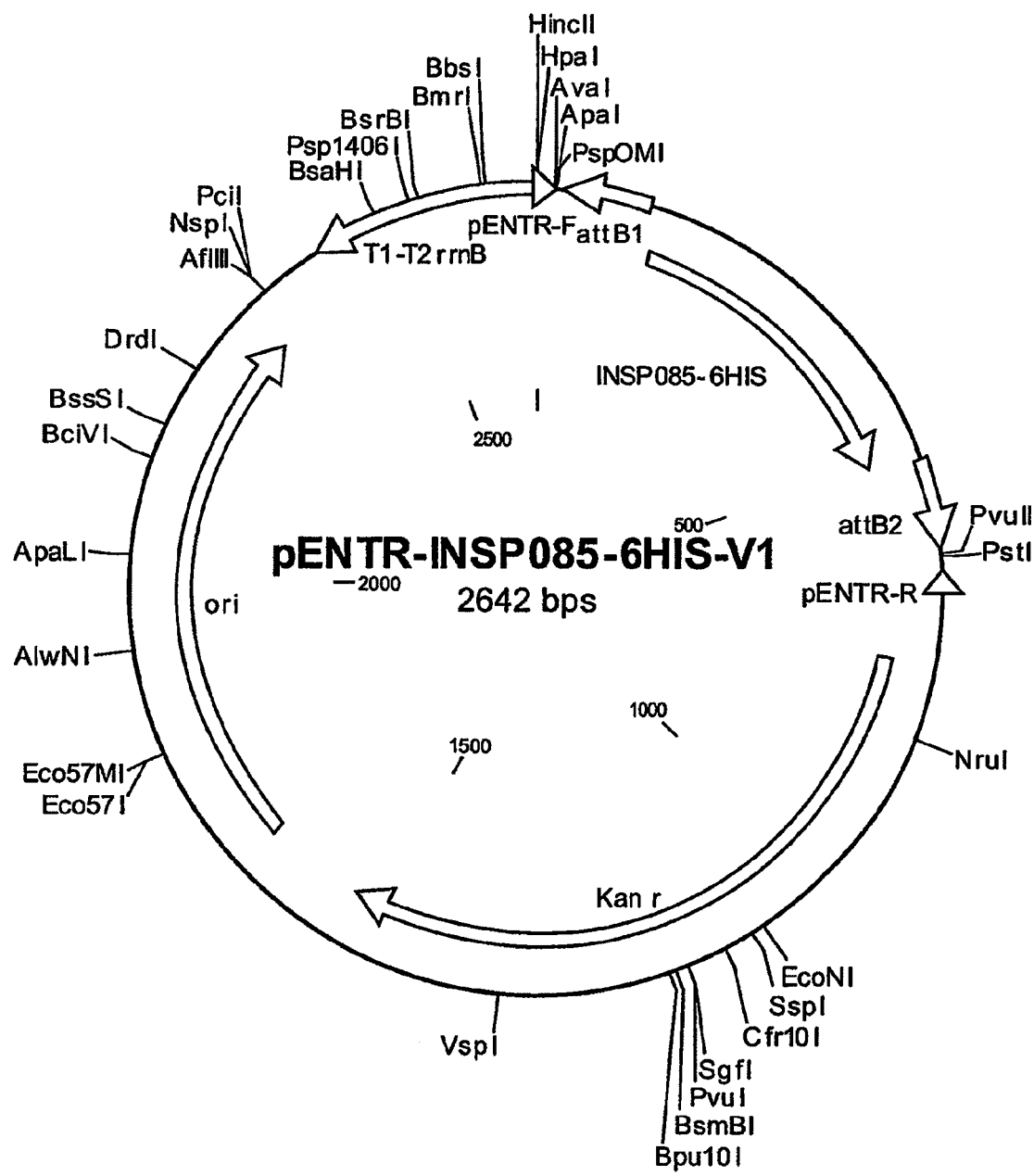
FIG. 7: Map of pENTR-INSP085-6HIS
Figure 8:
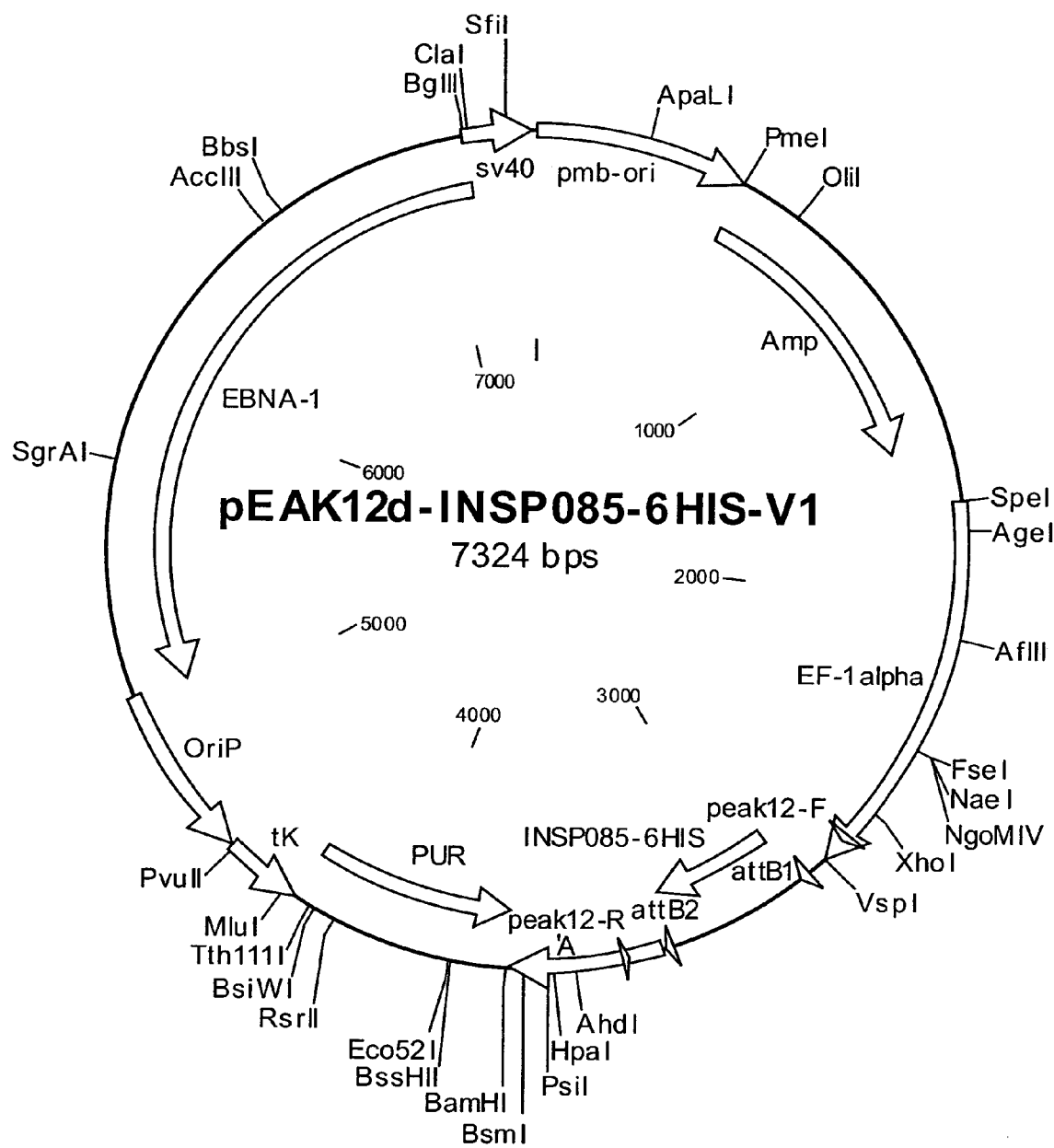
FIG. 8: Map of pEAK12d-INSP085-6HIS

The INSP085 polypeptide sequence, shown in SEQ ID NO:8, was used as a BLAST query against the NCBI non-redundant sequence database. As can be seen in FIG. 1, the top hit is for an inducible cytokine (chemokines were considered to be part of the cytokine family for a long time). The third to fifth hits are all for IL-8 precursors, thus providing further evidence that INSP085 is a member of the IL-8 like protein family.

Example 2

INSP085 Signal Sequence

FIGS. 3 and 4 show that INSP085 is predicted to posess a signal peptide at the start of the protein. As the data in FIG. 3 clearly shows, the signal peptide cleavage site is thought: to be between residues 16 and 17 of the INSP085 full protein sequence. FIG. 4 shows that this sequence is not an anchor peptide, so it is likely that INSP085 is a secreted protein (0.818 probability) Nielsen, H. et al. 1-1997, Protein Engineering, 10, 1-6; Nielsen, H., and Krogh, A.: Prediction of signal peptides and signal anchors by a hidden Markov model. In Proceedings of the Sixth International Conference on Intelligent Systems for Molecular Biology (ISMB 6), AAAI Press, Menlo Park, Calif., pp. 122-130 (1998)).

Example 3

Cloning of INSP085 by Exon Assembly

1. PCR Amplification of Exons Encoding INSP085 from Genomic DNA.

PCR primers were designed to amplify exons 1, 2 and 3 of INSP085 (table 1). The reverse primer for exon 1 (INSP085-exon1R) has an overlap of 18 bases with exon 2 of INSP085 at its 5' end. The forward primer for exon 2 (INSP085-exon2F) has an 18 bp overlap with exon 1 of INSP085 at its 5' end. The reverse primer for exon 2 (INSP085-exon2R) has an overlap of 18 bases with exon 3 at its 5' end. The forward primer for exon 3 (INSP085-exon3F) contains a 18 bp overlap with exon 2 at its 5' end.

To generate exon 1 of INSP085, the PCR reaction was performed in a final volume of 100 µl and contained 1.5 µl of genomic DNA (0.1µg/µl CLONTECH® cat. no. 65550-1), 2 µl of 10 mM dNTPs (AMERSHAM® Pharmacia Biotech), 6 µl of INSP085-exon1F (10 µM), 6 µl of INSP085-exon1R (10 µM), 5 µl of 10X Pfu buffer and 1 µl of Pfu polymerase (3U/µl) (PROMEGA® cat. no. M774B). The PCR conditions were 94° C. for 2 min; 35 cycles of 94° C. for 30s, 60° C. for 30s and 72° C. for 1 min; an additional elongation cycle of 72° C. for 5 min; and a holding cycle of 4° C. Reaction products were loaded onto a 1.5% agarose gel (1X TAE) and PCR products of the correct size (158 bp) were gel-purified using a QIAQUICK® Gel Extraction Kit (QIAGEN® cat. no. 28704) and eluted in 50 µl of elution buffer (QIAGEN®). Exon 1 was subcloned into pCR4 Blunt TOPO vector (INVITROGEN®) by incubating 4 µl of gel purified PCR product, with 1 µl of salt solution and 1 µl of topoisomerase modified PCR4 Blunt-TOPO vector.

The reaction mixture was incubated at RT for 30 min. An aliquot of this reaction (2 µl) was used to transform 50 µl of *E. coli* Top 10 multishot cells (INVITROGEN®) by heat shock as follows: cells and DNA were mixed in a 12 ml polypropylene tube. The mixture was stored on ice for 15 min then heat shocked at 42° C. for exactly 30 sec. Samples were then stored on ice for a further 2 min, then diluted by addition of 250 µl of room temperature SOC medium and incubated for 1 h. at 37° C. with shaking. Transformants (300 µl) were plated on LB plates containing 100 µg/ml of ampicillin and incubated over night at 37° C. Mini prep DNA was prepared from 5 ml cultures prepared from 30 of the resultant colonies using a Qiaprep Turbo 9600 robotic system (QIAGEN®). Mini-prep DNA was eluted in 50 µl of elution buffer. Plasmid mini prep DNA (200-500 ng) was then subjected to DNA sequencing with T7 and T3 sequencing primers using the BigDyeTerminator system (APPLIED BIOSYSTEMS® cat. no. 4390246) according to the manufacturer's instructions. Sequencing reactions were purified using Dye-Ex columns (QIAGEN®) or Montage SEQ 96 cleanup plates (Millipore cat. no. LSKS09624) then analyzed on an APPLIED BIOSYSTEMS® 3700 sequencer. One of the clones containing the correct sequence of exon 1 was then used as template for further amplification of exon 1 in a 50 µl PCR reaction containing 0.3 µl of miniprep DNA, 2 µl of 5 mM dNTPs (AMERSHAM® Pharmacia Biotech), 6 µl of INSP085-exon1F (10 µM), 6 µl of INBP085-exon1R (10 µM), 5 µl of 10X Pfu buffer and 0.5 µl of Pfu polymerase (3U/µl) (PROMEGA® cat. no. M774-B). The PCR conditions were 94° C. for 2 min; 30 cycles of 94° C. for 30s, 60° C. for 30s and 72° C. for 1 min; an additional elongation cycle of 72° C. for 3 min; and a holding cycle of 4° C. Reaction products were loaded onto a 1.5% agarose gel (1X TAE) and PCR products of the correct size (158bp) were gel-purified purified using a QIAQUICK® Gel Extraction Kit (QIAGEN® cat. no. 28704) and eluted in 30 µl of elution buffer (QIAGEN®).

To generate exon 2 of INSP085, the PCR reaction was performed in a final volume of 100 µl and contained 1.5 µl of human genomic DNA (0.1 µg/µl, NOVAGEN® cat. No. 69237), 2 µl of 10 mM dNTPs (AMERSHAM® Pharmacia Biotech), 6 µl of INSP085-exon2F (10 µM), 6 µl of INSP085-exon2R (10 µM), 5 µl of 10X Pwo buffer and 1 µl of Pwo polymerase (5U/µl) (Roche, cat. No. 1 644 955). The PCR conditions were 94° C. for 2 min; 35 cycles of 94° C. for 30s, 60° C. for 30s and 72° C. for 1 min; an additional elongation cycle of 72° C. for 5 min; and a holding cycle of 4° C. Reaction products were loaded onto a 1.5% agarose gel (1X TAE) and PCR products of the correct size (143 bp) were gel-purified using a QIAQUICK® Gel Extraction Kit (QIAGEN® cat. no. 28704) and eluted in 30 μl of elution buffer (QIAGEN®).

To generate exon 3 of INSP085, the PCR reaction was performed in a final volume of 100 μl and contained 1.5 μl of human genomic DNA (0.1 μg/μl, NOVAGEN® cat. No. 69237), 2 μl of 10 μM dNTPs (AMERSHAM® Pharmacia Biotech), 6 μl of INSP085-exon3F (10 μM), 6 μl of INSP085-exon3R (10 μM), 5 μl of 10X Pwo buffer and 1 μl Pwo polymerase (5U/μl ) (Roche, cat. No.1 644 955). The PCR conditions were 94° C. for 2 min; 35 cycles of 94° C. for 30s, 60° C. for 30s and 72° C. for 1 min; an additional elongation cycle of 72° C. for 5 min; and a holding cycle of 40° C. Reaction products were loaded onto a 1.5% agarose gel (1X TAE) and PCR products of the correct size (131 bp) were gel-purified using a QIAOUICK® Gel extraction Kit (QIAGEN® cat. no. 28704) and eluted in 30 μl of elution buffer (QIAGEN®).

2. Assembly of Exons 1-3 to Generate the INSP085 ORF

Exons 1, 2 and 3 were assembled in a 50 μl PCR reaction containing 2 μl of gel purified exon 1, 5 μl of gel purified exon 2, 5 μl of gel purified exon 3, 2 μl of 5 mM dNTPs, 6 μl of INSP085-E X1 (10 μM), 6 μl of INSP085EX2 (10 μM), 5 μl of 10X Pfu buffer, and 0.5 μl of Pfu polymerase (3U/μl) (PROMEGA®). The INSP085-EXI primer contains a partial attBI site and Kozak sequence at the 5' end. The INSPO 85-EX2 primer contains a 5HIS sequence at its 5' end. The reaction conditions were: 94° C., 4 min; 10 cycles of 94° C. for 30s, 48° C. for 30s and 70° C. for 2 min; 25 cycles of 94° C. for 30s, 52° C., for 30s and 70° C. for 2 min; an additional elongation step of 70° C. for 10 min; and a holding cycle at 4° C. Reaction products were analysed on a 1.5% agarose gel (1X TAE). PCR products of the correct size (387 bp) were gel purified using a QIAQUICK® Gel Extraction Kit (QIAGEN® cat. no. 28704) and eluted in 5 μl of elution buffer (QIAGEN®). The resultant PCR product contains the ORF of INSP085.

3. Subcloning of the INSP085 ORF Into pDONR201

The INSP085 ORF was subcloned into pDONR201 using the Gateway™ cloning system (INVITROGEN®). A partial attB1 recombination site was added to the 5' end of INSP085 ORF and a 6HIS tag sequence, stop codon and attB2 recombination site was added to the 3' end of the INSP085 ORF in a 50 μl PCR reaction containing 2 μl of gel purified INSP085-ORF PCR product, 2 μl of 5 mM dNTPs (AMERSHAM® Pharmacia Biotech), 6 μl of GCP-F (10 μM), 6 μl of GCP-R (10 μM), 5 μl of 10X Pfu buffer and 0.5 μl of Pfu polymerase (5U/μl) in a final volume of 50 μl. The PCR conditions were 94° C. for 2 min; 30 cycles of 94° C. for 30s; 55° C. for 30s and 72° C. for 1 min; an additional elongation step of 72° C. for 3 min and a holding cycle of 4° C. Reaction products were analysed on a 1.5% agarose gel (1X TAE) and PCR products of the correct size (445 bp, corresponding to Gateway-modified INSP085 ORF) were gel purified using a QIAQUICK® Gel Extraction Kit (QIAGEN® cat. no. 28704) and eluted in 50 μl of elution buffer (QIAGEN®). Gateway-modified INSP085 ORF was then transferred to pDONR201 using BP clonase as follows: 5 μl of Gateway-modified INSP085 ORF was incubated with 1.5 μl pDONR:201 (0.1 μg/μl), 2 μl BP buffer and 1.5 μl of BP 4. Subcloning of the INSP085 ORF to Expression Vector pEAK12d Plasmid eluate (1.5 μl) from a pDONR201 clone containing the correct sequence of the INSP085 ORF (pENTR-INSP085-6HIS, plasmid ID no. 13414, FIG. 4) was then used in a recombination reaction containing 1.5 μl pEAK12d vector (0.1 μg/μl), 2 μl LR buffer and 1.5 μl of LR clonase (INVITROGEN®) in a final volume of 10 μl. The mixture was incubated at RT for 1 h, stopped by addition of 1 μl proteinase K (2 μg) and incubated at 37° C. for a further 10 min. An aliquot of this reaction (1 μl) was used to transform 20 μl of *E. coli* DH10B cells (INVITROGEN®) (diluted ⅕ in sterile water) by electroporation using a Biorad Gene Pulser according to the manufacturer's recominendations. Electroporated cells were transferred to 12 ml polypropylene tubes, diluted by addition of 900 μl of room temperature SOC medium and incubated for 1 h at 37° C. with shaking. Transformants (100 μl) were plated on LB plates containing 100 μg/ml of ampicillin and incubated at 37° C. overnight. Mini prep DNA was prepared from 5 ml overnight cultures from 4 of the resultant colonies using a Qiaprep Turbo 9600 robotic system (QIAGEN®) as described above. Mini-prep DNA was eluted in 100 μl of elution buffer. Plasmid mini prep DNA (200-500 ng) was then subjected to DNA sequencing with pEAK12-F and pEAK12-R sequencing primers using the BigDyeTerminator system (APPLIED BIOSYSTEMS® cat. no. 4390246) according to the manufacturer's instructions. Sequencing reactions were purified using Dye-Ex columns (QIAGEN®) or Montage SEQ 96 cleanup plates (Millipore cat. no. LSKS09624) then analyzed on an APPLIED BIOSYSTEMS® 3700 sequencer.

CsCl gradient purified maxi-prep DNA was prepared from a 500 ml culture of a sequence verified clone, pEAK12d-INSP085-6HIS (plasmid ID no. 13413, FIG. 5) (Sambrook J. et al., in Molecular Cloning, a Laboratory Manual, $2^{nd}$ edition, 1989, Cold Spring Harbor Laboratory Press), resuspended at a concentration of 1 μg/μl in sterile water and stored at −20° C.

TABLE 1

Primers for INSP085 cloning and sequencing

| Primer | Sequence (5'-3') |
|---|---|
| GCP Forward | G GGG ACA AGT TTG TAC AAA AAA GCA GGC TTC GCC ACC |
| GCP Reverse | GGG GAC CAC TTT GTA CAA GAA AGC TGG GTT TCA *ATG GTG ATG GTG ATG GTG* |
| INSP085-exon1F | ATG AGC TTG GCT ATC CTC ATA TGG T |
| INSP085-exon1R | ATA CAC TGA CAT CCA ACT CTC ATG ACT TGC TTT GGC AAT A |

TABLE 1-continued

Primers for INSP085 cloning and sequencing

| Primer | Sequence (5'-3') |
|---|---|
| INSP085-exon2F | <mark>GCC AAA GCA AGT CAT GAG</mark> AGT TGG ATG TCA GTG TAT TC |
| INSP085-exon2R | <mark>CAA CAC ATA CCT TAT GTT</mark> TGA CTT CTT TTC TTC TGC AGA AA |
| INSP085-exon3F | <mark>GCA GAA GAA AAG AAG TCA</mark> AAC ATA AGG TAT GTG TTG CCT TA |
| INSP085-exon3R | TTA GCG TTT GTT ACC TGG GTT ATG AC |
| INSP085-EX1 | GCA GGC TTC <u>GCC ACC</u> ATG AGC TTG GCT ATC CTC AT |
| INSP085-EX2 | *GTG ATG GTG ATG GTG* GCG TTT GTT ACC TGG GTT AT |
| pEAK12-F | GCC AGC TTG GCA CTT GAT GT |
| pEAK12-R | GAT GGA GGT GGA CGT GTC AG |
| pENTR-F | TCG CGT TAA CGC TAG CAT GGA TCT C |
| pENTR-R | GTA ACA TCA GAG ATT TTG AGA CAC |
| T7 | TAA TAC GAC TCA CTA TAG GG |
| T3 | CTC COT TTA GTG AGG GTA ATT |

Underlined sequence = Kozak sequence
Bold = Stop codon
*Italic* sequence = His tag
Highlighted sequence = overlap with adjacent exon

Example 4

Expression and Purification of INSP085

Further experiments may now be performed to determine the tissue distribution and expression levels of the INSP085 polypeptides in vivo, on the basis of the nucleotide and amino acid sequence disclosed herein.

The presence of the transcripts for INSP085 may be investigated by PCR of cDNA from different human tissues. The INSP085 transcripts may be present at very low levels in the samples tested. Therefore, extreme care is needed in the design of experiments to establish the presence of a transcript in various human tissues as a small amount of genomic contamination in the RNA preparation will provide a false positive result. Thus, all RNA should be treated with DNAse prior to use for reverse transcription. In addition, for each tissue a control reaction may be set up in which reverse transcription was not undertaken (a-ve RT control).

For example, 1 µg of total RNA from each tissue may be used to generate cDNA using Multiscript reverse transcriptase (ABI®) and random hexamer primers. For each tissue, a control reaction is set up in which all the constituents are added except the reverse transcriptase (-ve RT control). PCR reactions are set up for each tissue on the reverse transcribed RNA samples and the minus RT controls. INSP085-specific primers may readily be designed on the basis of the sequence information provided herein. The presence of a product of the correct molecular weight in the reverse transcribed sample together with the absence of a product in the minus RT control may be taken as evidence for-the presence of a transcript in that tissue. Any suitable cDNA libraries may be used to screen for the INSP085 transcripts, not only those generated as described above.

The tissue distribution pattern of the INSP085 polypeptides will provide further useful information in relation to the function of those polypeptides.

In addition, further experiments may now be performed using the pEAK12d-INSP085-6HIS expression vectors. Transfection of mammalian cell lines with these vectors may enable the high level expression of the INSP085 proteins and thus enable the continued investigation of the functional characteristics of the INSP085 polypeptides. The following material and methods are an example of those suitable in such experiments:

Cell Culture

Human Embryonic Kidney 293 cells expressing the Epstein-Barr virus Nuclear Antigen (HEK293-EBNA, INVITROGEN®) are maintained in suspension in Ex-cell VPRO serum-free medium (seed stock, maintenance medium, JRH). Sixteen to 20 hours prior to transfection (Day-1), cells are seeded in 2×T225 flasks (50 ml per flask in DMEM/F12 (1:1) containing 2% FBS seeding medium (JRH) at a density of $2\times10^5$ cells/ml). The next day (transfection day 0) transfection takes place using the Jet PEI™ reagent (2 µl/µg of plasmid DNA, PolyPlus-transfection). For each flask, plasmid DNA is co-transfected with GFP (fluorescent reporter gene) DNA. The transfection mix is then added to the 2×T225 flasks and incubated at 37° C. (5% $CO_2$) for 6 days. Confirmation of positive transfection may be carried out by qualitative fluorescence examination at day 1 and day 6 (Axio-vert 10 ZEISS®).

On day 6 (harvest day), supernatants from the two flasks are pooled and centrifuged (e.g. 4° C., 400 g) and placed into a pot bearing a unique identifier. One aliquot (500 µl) is kept for QC of the 6His-tagged protein (internal bioprocessing QC).

Scale-up batches may be produced by following the protocol called "PEI transfection of suspension cells", referenced BP/PEI/HH(02/04, with PolyEthylenelmine from Polysciences as transfection agent.

Purification Process

The culture medium sample containing the recombinant protein with a C-terminal 6His tag is diluted with cold buffer A (50 mM $NaH_2PO_4$; 600 mM NaCl; 8.7% (w/v) glycerol, pH 7.5). The sample is filtered then through a sterile filter (MILLIPORE®) and kept at 4° C. in a sterile square media bottle (NALGENE®).

The purification is performed at 4° C. on the VISION workstation (APPLIED BIOSYSTEMS®) connected to an automatic sample loader (LABOMATIC®). The purification procedure is composed of two sequential steps, metal affinity chromatography on a Poros 20 MC (APPLIED BIOSYSTEMS®) column charged with Ni ions (4.6×50 mm, 0.83 ml), followed by gel filtration on a Sephadex G-25 medium (AMERSHAM® Pharmacia) column (1.0×10 cm).

For the first chromatography step the metal affinity column is regenerated with 30 column volumes of EDTA solution (100 mM EDTA; 1M NaCl; pH 8.0), recharged with Ni ions through washing with 15 column volumes of a 100 mM $NiSO_4$ solution, washed with 10 column volumes of buffer A, followed by 7 column volumes of buffer B (50 mM $NaH_2PO_4$; 600 mM NaCl; 8.7% (w/v) glycerol, 400 mN; imidazole, pH 7.5), and finally equilibrated with 15 column volumes of buffer A containing 15 mM imidazole. The sample is transferred, by the Labomatic sample loader, into a 200 ml sample loop and subsequently charged onto the Ni metal affinity column at a flow rate of 10 ml/min. The column is washed with 12 column volumes of buffer A, followed by 28 column volumes of buffer A containing 20 mM imidazole. During the 20 mM imidazole wash loosely attached contaminating proteins are eluted from the column. The recombinant His-tagged protein is finally eluted with 10 column volumes of buffer B at a flow rate of 2 ml/min, and the eluted protein is collected.

For the second chromatography step, the SEPHADEX® G-25 gel-filtration column is regenerated with 2 ml of buffer D (1.137 M NaCl; 2.7 mM KCl; 1.5 mM $KH_2PO_4$, 8 mM $Na_2HPO_4$ $_{pH}$ 7.2) and subsequently equilibrated with 4 column volumes of buffer C (137 mM NaCl; 2.7 mM KCl; 1.5 mM $KH_2PO_4$; 8 mM $Na_2HPO_4$; 20% (w/v) glycerol; pH 7.4). The peak fraction eluted from the Ni-column is automatically loaded onto the SEPHADEX® G-25 column through the integrated sample loader on the VISION and the protein is eluted with buffer C at a flow rate of 2 ml/min. The fraction was filtered through a sterile centrifugation filter (MILLIPORE®), frozen and stored at -80° C. An aliquiot of the sample is analyzed on SDS-PAGE (4-12% NuPAGE gel; NOVEX®) Western blot with anti-His antibodies. The NuPAGE gel may be stained in a 0.1% Coomassie blue R250 staining solution (30% methanol, 10% acetic acid) at room temperature for 1 h and subsequently destained in 20% methanol, 7.5% acetic acid until the background is clear and the protein bands clearly visible.

Following the electrophoresis the proteins are electrotransferred from the gel to a nitrocellulose membrane. The membrane is blocked with 5% milk powder in buffer E (137 mM NaCl; 2.7 mM KCl; 1.5 mM $KH_2PO_4$; 8 mM $Na_2HPO_4$; 0.1% Tween 20, pH 7.4) for 1 h at room temperature, and subsequently incubated with a mixture of 2 rabbit polyclonal anti-His antibodies (G-18 and H-15, 0.2 µg/ml each; Santa Cruz) in 2.5% milk powder in buffer E overnight at 4° C. After a further 1 hour incubation at room temperature, the membrane is washed with buffer E (3×10 min), and then incubated with a secondary HRP-conjugated anti-rabbit antibody (DAKO, HRP 0399) diluted 1/3000 in buffer E containing 2.5% milk powder for 2 hours at room temperature. After washing with buffer E (3×10 minutes), the membrane is developed with the ECL kit (AMERSHAM® Pharmacia) for 1 min. The membrane is subsequently exposed to a Hyperfilm (AMERSHAM® Pharmacia), the film developed and the western blot image visually analysed.

For samples that showed detectable protein bands by Coomassie staining, the protein concentration may be determined using the BCA protein assay kit (PIERCE™) with bovine serum albumin as standard.

Furthermore, overexpression or knock-down of the expression of the polypeptides in cell lines may be used to determine the effect on transcriptional activation of the host cell genome. Dimerisation partners, co-activators and co-repressors of the INSP085 polypeptide may be identified by immunoprecipitation combined with Western blotting and immunoprecipitation combined with mass spectroscopy.

---

List of INSP085 specific sequences

```
(Sequence Listing):
SEQ ID NO:1 (INSP085 Nucleotide sequence exon 1)
   1 ATGAGCTTGG CTATCCTCAT ATGGTGGCAG CTGCATTTTA ACAGAGCAGG GGTAGAAACT
  61 CCTAGGCTTC TTACCTTGTT GGCCTGGAAC ATCTACATCA TCACTTTTAA CACTTCCTAT
 121 TGGCCAAAGC AAGTCATGAG SEQ ID NO:2 (INSP085 Protein sequence exon 1)
   1 MSLAILIWWQ LHFNRAGVET PRLLTLLAWN IYIITFNTSY WPKQVMR SEQ ID NO:3 (INSP085 Nucleotide sequence exon 2)
   1 AGTTGGATGT CAGTGTATTC AGACACATTC TGACTTTATT CCTCACCAAT TCATTAAAAA
  61 TGATCAGTTG ATACATAAGG ATCCTTTCTG CAGAAGAAAA GAAGTCA SEQ ID NO:4 (INSP085 Protein sequence exon 2)
   1 VGCQCIQTHS DFIPHQFIKN DQLIHKDPFC RRKEVK SEQ ID NO:5 (INSP085 Nucleotide sequence exon 3)
   1 AACATAAGGT ATGTGTTGCC TTAATTGCTT GTATAGTTGA GGTAAAAATT GTTGGCCAGA
  61 AAATAGTCTG GAATCATTTT AGAAGTTGTC ATAACCCAGG TAACAAACGC TAA SEQ ID NO:6 (INSP085 Protein sequence exon 3)
   1 HKVCVALIAC IVEVKIVGQK IVWNHFRSCH NPGNKR SEQ ID NO:7 (INSP085 Nucleotide sequence)
   1 ATGAGCTTGG CTATCCTCAT ATGGTGGCAG CTGCATTTTA ACAGAGCAGG GGTAGAAACT
  61 CCTAGGCTTC TTACCTTGTT GGCCTGGAAC ATCTACATCA TCACTTTTAA CACTTCCTAT
 121 TGGCCAAAGC AAGTCATGAG AGTTGGATGT CAGTGTATTC AGACACATTC TGACTTTATT
 181 CCTCACCAAT TCATTAAAAA TGATCAGTTG ATACATAAGG ATCCTTTCTG CAGAAGAAAA
 241 GAAGTCAAAC ATAAGGTATG TGTTGCCTTA ATTGCTTGTA TAGTTGAGGT AAAAATTGTT
 301 GGCCAGAAAA TAGTCTGGAA TCATTTTAGA AGTTGTCATA ACCCAGGTAA CAAACGCTAA
```

-continued

List of INSP085 specific sequences

SEQ ID NO:8 (INSP085 Protein sequence)
  1 MSLAILIWWQ LHFNRAGVET PRLLTLLAWN IYIITFNTSY WPKQVMRVGC QCIQTHSDFI
 61 PHQFIKNDQL IHKDPFCRRK EVKHKVCVAL IACIVEVKIV GQKIVWNHFR SCHNPGNKR SEQ ID NO:9 (INSP085 exon 1 mature nucleotide sequence)
  1 GGGGTAGAAA CTCCTAGGCT TCTTACCTTG TTGGCCTGGA ACATCTACAT CATCACTTTT
 61 AACACTTCCT ATTGGCCAAA GCAAGTCATG AG SEQ ID NO:10 (INSP085 exon 1 mature protein sequence)
  1 GVETPRLLTL LAWNIYIITF NTSYWPKQVM R SEQ ID NO:11 (INSP085 mature nucleotide sequence)
  1 GGGGTAGAAA CTCCTAGGCT TCTTACCTTG TTGGCCTGGA ACATCTACAT CATCACTTTT
 61 AACACTTCCT ATTGGCCAAA GCAAGTCATG AGAGTTGGAT GTCAGTGTAT TCAGACACAT
121 TCTGACTTTA TTCCTCACCA ATTCATTAAA AATGATCAGT TGATACATAA GGATCCTTTC
181 TGCAGAAGAA AAGAAGTCAA ACATAAGGTA TGTGTTGCCT TAATTGCTTG TATAGTTGAG
241 GTAAAAATTG TTGGCCAGAA AATAGTCTGG AATCATTTTA GAAGTTGTCA TAACCCAGGT
301 AACAAACGCT AA SEQ ID NO:12 (INSP085 mature protein sequence)
  1 GVETPRLLTL LAWNIYIITF NTSYWPKQVM RVGCQCIQTH SDFIPHQFIK NDQLIHKDPF
 61 CRRKEVKHKV CVALIACIVE VKIVGQKIVW NHFRSCHNPG NKR The invention will now be further described by the following numbered paragraphs:

A. A polypeptide, which polypeptide:
  (i) comprises the amino acid sequence as recited in SEQ ID NO:2, SEQ ID NO:4, SEQ ID NO:6, SEQ ID NO:8, SEQ ID NO:10 and/or SEQ ID NO:12;
  (ii) is a fragment thereof which functions as a member of the IL-8 like chemokine family, or having an antigenic determinant in cominon with the polypeptide of (i); or
  (iii) is a functional equivalent of (i) or (ii).

B. A polypeptide according to paragraph 1 which:
  (i) comprises the amino acid sequence as recited in SEQ ID NO:8, SEQ ID NO:10, or SEQ IID NO:12;
  (ii) is a fragment thereof which functions as a member of the IL-8 like chemokine family, or having an antigenic determinant in common with the polypeptide of (i); or
  (iii) is a functional equivalent of (i) or (ii).

C. A polypeptide according to paragraph A or B which:
  (i) consists of the amino acid sequence as recited in SEQ ID NO:2, SEQ ID NO:4, SEQ ID NO:6, SEQ ID NO:8, SEQ ID NO:10, and/or SEQ ID NO:12;
  (ii) is a fragment thereof which functions as a member of the IL-8 like chemokine family, or having an antigenic determinant in common with the polypeptide of (i); or
  (iii) is a functional equivalent of (i) or (ii).

D. A polypeptide which is a function equivalent according to part (iii) of any of the above paragraphs, characterized in that it is homologous to the amino acid sequence as recited in SEQ ID NO:2, SEQ ID NO:4, SEQ ID NO:6, SEQ ID NO:8, SEQ ID NO:10 or SEQ ID NO:12 and is a member of the IL-8 like chemokine family.

E. A polypeptide which is a fragment or a functional equivalent as recited in any one of paragraphs A to D, which has greater than 80% sequence identity with the amino acid sequence recited in SEQ ID NO:2, SEQ ID NO:4, SEQ ID NO:6, SEQ ID NO:8, SEQ ID NO:10 or SEQ ID NO:12 or with an active fragment thereof, preferably greater than 85%, 90%, 95%, 98% or 99% sequence identity.

F. A polypeptide which is a functional equivalent as recited in any one of paragraphs A to E which exhibits significant structural homology with a polypeptide having the amino acid sequence recited in SEQ ID NO:2, SEQ ID NO:4, SEQ ID NO:6, SEQ ID NO:8, SEQ ID NO:10 or SEQ ID NO:12.

G. A polypeptide which is a fragment as recited in paragraphs A-C and paragraph E having an antigenic determinant in common with the polypeptide of part (i) of any one of paragraph A to paragraph C which consists of 7 or more amino acid residues from the amino acid sequence recited in SEQ ID NO:2, SEQ ID NO:4, SEQ ID NO:6, SEQ ID NO:8, SEQ ID NO:10 or SEQ ID NO:12.

H. A purified nucleic acid molecule which encodes a polypeptide according to any one of the preceeding paragraphs.

I. A purified nucleic acid molecule according to paragraph H, which comprise the nucleic acid sequence as recited in SEQ ID NO:1, SEQ ID NO:3, SEQ ID NO:5, SEQ ID NO:7, SEQ ID NO:9, and/or SEQ ID NO:11, or is a redundant equivalent or fragment thereof.

J. A purified nucleic acid molecule according to paragraph H or paragraph I which consists of the nucleic acid sequence as recited in SEQ ID NO:1, SEQ ID NO:3, SEQ ID NO:5, SEQ ID NO:7, SEQ ID NO:9 and/or SEQ ID NO:11, or is a redundant equivalent or fragment thereof.

K. A purified nucleic acid molecule which hybridizes under high stringency conditions with a nucleic acid molecule according to any one of paragraphs H to J.

L. A vector comprising an nucleic acid molecule as recited in any one of paragraphs H to K.

M. A host cell transformed with a vector according to paragraph L.

N. A ligand which binds specifically to the IL-8 like chemokine polypeptide according to any one of paragraphs A to G.

O. A ligand according to paragraph N, which is an antibody.

P. A compound that either increases or decreases the level of expression or activity of a polypeptide according to any one of paragraphs A to G.

Q. A compound according to paragraph P that binds to a polypeptide according to any one of paragraphs A to G without inducing any of the biological effects of the polypeptide.

R. A compound according to paragraph Q, which is a natural or modified substrate, ligand, enzyme, receptor or structural or functional mimetic.

S. A polypeptide according to any one of paragraphs A to G a nucleic acid molecule according to any one of paragraphs H to K a vector according to paragraph L, a host cell according to paragraph M, a ligand according to paragraph N or paragraph O, or a compound according to any one of paragraphs P to R for use in therapy or diagnosis of disease.

T. A method of diagnosing a disease, in a patient, comprising assessing the level of expression of a natural gene encoding a polypeptide according to any one of paragraphs A to G, or assessing the activity of a polypeptide according to any one of paragraphs A to G, in tissue from said patient and comparing said level of expression or activity to a control level, wherein a level that is different to said control level is indicative of disease.

U. A method according to paragraph T that is carried out in vitro.

V. A method according to paragraph T or paragraph U, which comprises the steps of:
 (a) contacting a ligand according to paragraph N or paragraph O with a biological sample under conditions suitable for the formation of a ligand-polypeptide complex; and (b) detecting said complex.

W. A method according to paragraph T or paragraph U, comprising the steps of:
 a) contacting a sample of tissue from the patient with a nucleic acid probe under stringent conditions that allow the formation of a hybrid complex between a nucleic acid molecule according to any one of paragraphs H to K and the probe;
 b) contacting a control sample with said probe under the same conditions used in step a); and
 c) detecting the presence of hybrid complexes in said samples; wherein detection of levels of the hybrid complex in the patient sample that differ from levels of the hybrid complex in the control sample is indicative of disease.

X. A method according to paragraph T or paragraph U, comprising:
 a) contacting a sample of nucleic acid from tissue of the patient with a nucleic acid primer under stringent conditions that allow the formation of a hybrid complex between a nucleic acid molecule according to any one of paragraphs H to K and the primer;
 b) contacting a control sample with said primer under the same conditions used in step a);
 c) amplifying the sampled nucleic acid; and
 d) detecting the level of amplified nucleic acid from both patient and control samples;

wherein detection of levels of the amplified nucleic acid in the patient sample that differ significantly from levels of the amplified nucleic acid in the control sample is indicative of disease.

Y. A method according to paragraph T or paragraph U comprising:
 a) obtaining a tissue sample from a patient being tested for disease;
 b) isolating a nucleic acid molecule according to any one of paragraphs H to K from said tissue sample; and
 c) diagnosing the patient for disease by detecting the presence of a mutation which is associated with disease in the nucleic acid molecule as an indication of the disease.

Z. The method of paragraph Y, further comprising amplifying the nucleic acid molecule to form an amplified product and detecting the presence or absence of a mutation in the amplified product.

AA. The method of paragraph Y or paragraph Z, wherein the presence or absence of the mutation in the patient is detected by contacting said nucleic acid molecule with a nucleic acid probe that hybridises to said nucleic acid molecule under stringent conditions to form a hybrid double-stranded molecule, the hybrid double-stranded molecule having an unhybridised portion of the nucleic acid probe strand at any portion corresponding to a mutation associated with disease; and detecting the presence or absence of an unhybridised portion of the probe strand as an indication of the presence or absence of a disease-associated mutation.

AB. A method according to any one of paragraphs T to AA, wherein said disease includes, but is not limited to, reproductive disorders, including infertility, cell proliferative disorders, including neoplasm, melanoma, lung, colorectal, breast, pancreas, head and neck and other solid tumours; myeloproliferative disorders, such as leukemia, non-Hodgkin lymphoma, leukopenia, thrombocytopenia, angiogenesis disorder, Kaposis' sarcoma; autoimmune/inflammatory disorders, including allergy, inflammatory bowel disease, arthritis, psoriasis and respiratory tract inflammation, asthma, and organ transplant rejection; cardiovascular disorders, including hypertension, oedema, angina, atherosclerosis, thrombosis, sepsis, shock, reperflision injury, and ischemia; neurological disorders including central nervous system disease, Alzheimer's disease, brain injury, amyotrophic lateral sclerosis, and pain; developmental disorders; metabolic disorders including diabetes mellitus, osteoporosis, and obesity, AIDS and renal disease; infections including viral infection, bacterial infection, fungal infection, parasitic infection, rheumatoid arthritis (RA), psoriatic arthritis, osteoarthritis, systemic lupus erythematosus (SLE), systemic sclerosis, scleroderma, polymyositis, glomerulonephritis, fibrosis, lung fibrosis and inflammation, allergic, or hypersensitvity diseases, dermatitis, asthma, chronic obstructive pulmonary disease, (COPD), Crohn's disease, ulcerative colitis, multiple sclerosis, septic shock, HIV infection, transplant rejection, wound healing, metastasis, endometriosis, hepatitis, liver fibrosis, cancer, analgesia, and vascular inflammation related to atherosclerosis.

AC. A method according to any one of paragraphs T to AA, wherein said disease is a disease in which IL-8 like chemokines are implicated.

AD. Use of a polypeptide according to any one of paragraphs A to G as an IL-8 like chemokine protein.

AE. A pharmaceutical composition comprising a polypeptide according to any one of paragraphs A to G, a nucleic acid molecule according to any one of paragraphs H to K, a vector according to paragraph L, a host cell according to paragraph M, a ligand according to paragraph N or paragraph O, or a compound according to any one of paragraphs P to R.

AF. A vaccine composition comprising a polypeptide according to any one of paragraphs A to G or a nucleic acid molecule according to any one of paragraphs H to K.

AG. A polypeptide according to any one of paragraphs A to G, a nucleic acid molecule according to any one of paragraphs H to K, a vector according to paragraph L, a host cell according to paragraph M, a ligand according to paragraph N or paragraph O, a compound according to any one of paragraphs P to R, or a pharmaceutical composition according to paragraph AE, for use in the manufacture of a medicament for the treatment of reproductive disorders, including infertility, cell proliferative disorders, including neoplasm, melanoma, lung, colorectal, breast, pancreas, head and neck and other solid tumours; myeloproliferative disorders, such as leukemia, non-Hodgkin lymphoma, leukopenia, thrombocytopenia, angiogenesis disorder, Kaposi' sarcoma; autoimmune/inflammatory disorders, including allergy, inflammatory bowel disease, arthritis, psoriasis and respiratory tract inflammation, asthma, and organ transplant rejection; cardiovascular disorders, including hypertension, oedema, angina, atherosclerosis, thrombosis, sepsis, shock, reperflision injury, and ischemia; neurological disorders including central nervous system disease, Alzheimer's disease, brain injury, amyotrophic lateral sclerosis, and pain; developmental disorders; metabolic disorders including diabetes mellitus, osteoporosis, and obesity, AIDS and renal disease; infections including viral infection, bacterial infection, fungal infection, parasitic infection, rheumatoid arthritis (RA), psoriatic arthritis, osteoarthritis, systemic lupus erythematosus (SLE), systemic sclerosis, scleroderma, polymyositis, glomerulonephritis, fibrosis, lung fibrosis and inflamination, allergic, or hypersensitvity diseases, dermatitis, asthma, chronic obstructive pulmonary disease, (COPD), Crohn's disease, ulcerative colitis, multiple sclerosis, septic shock, HTV infection, transplant rejection, wound healing, metastasis, endometriosis, hepatitis, liver fibrosis, cancer, analgesia, and vascular inflammation related to atherosclerosis, and other pathological conditions.

AH. A polypeptide according to any one of paragraphs A to G, a nucleic acid molecule according to any one of paragraphs H to K, a vector according to paragraph L, a host cell according to paragraph M, a ligand according to paragraph N or paragraph O, a compound according to any one of paragraphs P to R, or a pharmaceutical composition according to paragraph AE, for use in the manufacture of a medicament for the treatment of a disease in which like chemokines are implicated.

AI. A method of treating a disease in a patient, comprising administering to the patient a polypeptide according to any one of paragraphs A to G, a nucleic acid molecule according to any one of paragraphs H to K, a vector according to paragraph L, a host cell according to paragraph M, a ligand according to paragraph N or paragraph O, a compound according to any one of paragraphs P to R, or a pharmaceutical composition according to paragraph AE.

AJ. A method according to paragraph AI, wherein, for diseases in which the expression of the natural gene or the activity of the polypeptide is lower in a diseased patient when compared to the level of expression or activity in a healthy patient, the polypeptide, nucleic acid molecule, vector, ligand, compound or composition administered to the patient is an agonist.

AK. A method according to paragraph AI, wherein, for diseases in which the expression of the natural gene or activity of the polypeptide is higher in a diseased patient when compared to the level of expression or activity in a healthy patient, the polypeptide, nucleic acid molecule, vector, ligand, compound or composition administered to the patient is an antagonist.

AL. A method of monitoring the therapeutic treatment of disease in a patient, comprising monitoring over a period of time the level of expression or activity of a polypeptide according to any one of paragraphs A to G, or the level of expression of a nucleic acid molecule according to any one of paragraphs H to K in tissue from said patient, wherein altering said level of expression or activity over the period of time towards a control level is indicative of regression of said disease.

AM. A method for the identification of a compound that is effective in the -treatment and/or diagnosis of disease, comprising contacting a polypeptide according to any one of paragraphs A to G, or a nucleic acid molecule according to any one of paragraphs H to K with one or more compounds suspected of possessing binding affinity for said polypeptide or nucleic acid molecule, and selecting a compound that binds specifically to said nucleic acid molecule or polypeptide.

AN. A kit useful for diagnosing disease comprising a first container containing a nucleic acid probe that hybridises under stringent conditions with a nucleic acid molecule according to any one of paragraphs H to K; a second container containing primers useful for amplifying said nucleic acid molecule; and instructions for using the probe and primers for facilitating the diagnosis of disease.

AO. The kit of paragraph AN, further comprising a third container holding an agent for digesting unhybridised RNA.

AP. A kit comprising an array of nucleic acid molecules, at least one of which is a nucleic acid molecule according to any one of paragraphs H to K.

AQ. A kit comprising one or more antibodies that bind to a polypeptide as recited in any one of paragraphs A to G; and a reagent useful for the detection of a binding reaction between said antibody and said polypeptide.

AR. A transgenic or knockout non-human animal that has been transformed to express higher, lower or absent levels of a polypeptide according to any one of paragraphs A to G.

AS. A method for screening for a compound effective to treat disease, by contacting a nonhuman transgenic animal according to paragraph AR with a candidate compound and determining the effect of the compound on the disease of the animal.

The invention claimed is:

1. An isolated polypeptide, which comprises the amino acid sequence as recited in SEQ ID NO:2, SEQ ID NO:4, SEQ ID NO:6, SEQ ID NO:8, SEQ ID NO:10 and/or SEQ ID NO:12.

2. An isolated polypeptide which has greater than 95% sequence identity with the amino acid sequence recited in SEQ ID NO:2, SEQ ID NO:4, SEQ ID NO:6, SEQ ID NO:8, SEQ ID NO:10 or SEQ ID NO:12 and which functions as a member of the IL-8 like chemokine family.

3. A composition comprising an isolated polypeptide according to claim 1.

* * * * *

SEQUENCE LISTING

<160> NUMBER OF SEQ ID NOS: 28

<210> SEQ ID NO 1
<211> LENGTH: 140
<212> TYPE: DNA
<213> ORGANISM: Homo sapiens

<400> SEQUENCE: 1

-continued

```
atgagcttgg ctatcctcat atggtggcag ctgcattta acagagcagg ggtagaaact    60
cctaggcttc ttaccttgtt ggcctggaac atctacatca tcacttttaa cacttcctat   120
tggccaaagc aagtcatgag                                               140
```

<210> SEQ ID NO 2
<211> LENGTH: 47
<212> TYPE: PRT
<213> ORGANISM: Homo sapiens

<400> SEQUENCE: 2

Met Ser Leu Ala Ile Leu Ile Trp Trp Gln Leu His Phe Asn Arg Ala
1               5                   10                  15

Gly Val Glu Thr Pro Arg Leu Leu Thr Leu Leu Ala Trp Asn Ile Tyr
            20                  25                  30

Ile Ile Thr Phe Asn Thr Ser Tyr Trp Pro Lys Gln Val Met Arg
        35                  40                  45

<210> SEQ ID NO 3
<211> LENGTH: 107
<212> TYPE: DNA
<213> ORGANISM: Homo sapiens

<400> SEQUENCE: 3

```
agttggatgt cagtgtattc agacacattc tgactttatt cctcaccaat tcattaaaaa    60
tgatcagttg atacataagg atcctttctg cagaagaaaa gaagtca                 107
```

<210> SEQ ID NO 4
<211> LENGTH: 36
<212> TYPE: PRT
<213> ORGANISM: Homo sapiens

<400> SEQUENCE: 4

Val Gly Cys Gln Cys Ile Gln Thr His Ser Asp Phe Ile Pro His Gln
1               5                   10                  15

Phe Ile Lys Asn Asp Gln Leu Ile His Lys Asp Pro Phe Cys Arg Arg
            20                  25                  30

Lys Glu Val Lys
        35

<210> SEQ ID NO 5
<211> LENGTH: 113
<212> TYPE: DNA
<213> ORGANISM: Homo sapiens

<400> SEQUENCE: 5

```
aacataaggt atgtgttgcc ttaattgctt gtatagttga ggtaaaaatt gttggccaga    60
aaatagtctg gaatcatttt agaagttgtc ataacccagg taacaaacgc taa          113
```

<210> SEQ ID NO 6
<211> LENGTH: 36
<212> TYPE: PRT
<213> ORGANISM: Homo sapiens

<400> SEQUENCE: 6

His Lys Val Cys Val Ala Leu Ile Ala Cys Ile Val Glu Val Lys Ile
1               5                   10                  15

Val Gly Gln Lys Ile Val Trp Asn His Phe Arg Ser Cys His Asn Pro
            20                  25                  30

Gly Asn Lys Arg

<210> SEQ ID NO 7
<211> LENGTH: 360
<212> TYPE: DNA
<213> ORGANISM: Homo sapiens

<400> SEQUENCE: 7

```
atgagcttgg ctatcctcat atggtggcag ctgcatttta acagagcagg ggtagaaact      60
cctaggcttc ttaccttgtt ggcctggaac atctacatca tcacttttaa cacttcctat     120
tggccaaagc aagtcatgag agttggatgt cagtgtattc agacacattc tgactttatt     180
cctcaccaat tcattaaaaa tgatcagttg atacataagg atcctttctg cagaagaaaa     240
gaagtcaaac ataaggtatg tgttgcctta attgcttgta tagttgaggt aaaaattgtt     300
ggccagaaaa tagtctggaa tcattttaga agttgtcata acccaggtaa caaacgctaa     360
```

<210> SEQ ID NO 8
<211> LENGTH: 119
<212> TYPE: PRT
<213> ORGANISM: Homo sapiens

<400> SEQUENCE: 8

Met Ser Leu Ala Ile Leu Ile Trp Trp Gln Leu His Phe Asn Arg Ala
1               5                   10                  15
Gly Val Glu Thr Pro Arg Leu Leu Thr Leu Leu Ala Trp Asn Ile Tyr
            20                  25                  30
Ile Ile Thr Phe Asn Thr Ser Tyr Trp Pro Lys Gln Val Met Arg Val
        35                  40                  45
Gly Cys Gln Cys Ile Gln Thr His Ser Asp Phe Ile Pro His Gln Phe
    50                  55                  60
Ile Lys Asn Asp Gln Leu Ile His Lys Asp Pro Phe Cys Arg Arg Lys
65                  70                  75                  80
Glu Val Lys His Lys Val Cys Val Ala Leu Ile Ala Cys Ile Val Glu
                85                  90                  95
Val Lys Ile Val Gly Gln Lys Ile Val Trp Asn His Phe Arg Ser Cys
            100                 105                 110
His Asn Pro Gly Asn Lys Arg
        115

<210> SEQ ID NO 9
<211> LENGTH: 92
<212> TYPE: DNA
<213> ORGANISM: Homo sapiens

<400> SEQUENCE: 9

```
ggggtagaaa ctcctaggct tcttaccttg ttggcctgga acatctacat catcactttt      60
aacacttcct attggccaaa gcaagtcatg ag                                    92
```

<210> SEQ ID NO 10
<211> LENGTH: 31
<212> TYPE: PRT
<213> ORGANISM: Homo sapiens

<400> SEQUENCE: 10

Gly Val Glu Thr Pro Arg Leu Leu Thr Leu Leu Ala Trp Asn Ile Tyr
1               5                   10                  15
Ile Ile Thr Phe Asn Thr Ser Tyr Trp Pro Lys Gln Val Met Arg
            20                  25                  30

<210> SEQ ID NO 11
<211> LENGTH: 312
<212> TYPE: DNA
<213> ORGANISM: Homo sapiens

<400> SEQUENCE: 11

```
ggggtagaaa ctcctaggct tcttaccttg ttggcctgga acatctacat catcactttt      60
aacacttcct attggccaaa gcaagtcatg agagttggat gtcagtgtat tcagacacat     120
tctgacttta ttcctcacca attcattaaa aatgatcagt tgatacataa ggatcctttc     180
tgcagaagaa aagaagtcaa acataaggta tgtgttgcct taattgcttg tatagttgag     240
gtaaaaattg ttggccagaa aatagtctgg aatcatttta gaagttgtca taacccaggt     300
aacaaacgct aa                                                         312
```

<210> SEQ ID NO 12
<211> LENGTH: 103
<212> TYPE: PRT
<213> ORGANISM: Homo sapiens

<400> SEQUENCE: 12

```
Gly Val Glu Thr Pro Arg Leu Leu Thr Leu Leu Ala Trp Asn Ile Tyr
1               5                   10                  15

Ile Ile Thr Phe Asn Thr Ser Tyr Trp Pro Lys Gln Val Met Arg Val
                20                  25                  30

Gly Cys Gln Cys Ile Gln Thr His Ser Asp Phe Ile Pro His Gln Phe
            35                  40                  45

Ile Lys Asn Asp Gln Leu Ile His Lys Asp Pro Phe Cys Arg Arg Lys
        50                  55                  60

Glu Val Lys His Lys Val Cys Val Ala Leu Ile Ala Cys Ile Val Glu
65                  70                  75                  80

Val Lys Ile Val Gly Gln Lys Ile Val Trp Asn His Phe Arg Ser Cys
                85                  90                  95

His Asn Pro Gly Asn Lys Arg
            100
```

<210> SEQ ID NO 13
<211> LENGTH: 37
<212> TYPE: DNA
<213> ORGANISM: Artificial Sequence
<220> FEATURE:
<223> OTHER INFORMATION: Primer GCP Forward

<400> SEQUENCE: 13

```
ggggacaagt ttgtacaaaa aagcaggctt cgccacc                               37
```

<210> SEQ ID NO 14
<211> LENGTH: 51
<212> TYPE: DNA
<213> ORGANISM: Artificial Sequence
<220> FEATURE:
<223> OTHER INFORMATION: Primer GCP reverse

<400> SEQUENCE: 14

```
ggggaccact ttgtacaaga aagctgggtt tcaatggtga tggtgatggt g               51
```

<210> SEQ ID NO 15
<211> LENGTH: 25
<212> TYPE: DNA
<213> ORGANISM: Artificial Sequence

```
<220> FEATURE:
<223> OTHER INFORMATION: Primer INSP085-exon1F

<400> SEQUENCE: 15
atgagcttgg ctatcctcat atggt                                          25

<210> SEQ ID NO 16
<211> LENGTH: 41
<212> TYPE: DNA
<213> ORGANISM: Artificial Sequence
<220> FEATURE:
<223> OTHER INFORMATION: Primer INSP085-exon1R

<400> SEQUENCE: 16
atacactgac atccaactct catgacttgc tttggccaat a                        41

<210> SEQ ID NO 17
<211> LENGTH: 38
<212> TYPE: DNA
<213> ORGANISM: Artificial Sequence
<220> FEATURE:
<223> OTHER INFORMATION: Primer INSP085-exon2F

<400> SEQUENCE: 17
gccaaagcaa gtcatgagag ttggatgtca gtgtattc                            38

<210> SEQ ID NO 18
<211> LENGTH: 41
<212> TYPE: DNA
<213> ORGANISM: Artificial Sequence
<220> FEATURE:
<223> OTHER INFORMATION: Primer INSP085-exon2R

<400> SEQUENCE: 18
caacacatac cttatgtttg acttcttttc ttctgcagaa a                        41

<210> SEQ ID NO 19
<211> LENGTH: 41
<212> TYPE: DNA
<213> ORGANISM: Artificial Sequence
<220> FEATURE:
<223> OTHER INFORMATION: Primer INSP085-exon3F

<400> SEQUENCE: 19
gcagaagaaa agaagtcaaa cataaggtat gtgttgcctt a                        41

<210> SEQ ID NO 20
<211> LENGTH: 26
<212> TYPE: DNA
<213> ORGANISM: Artificial Sequence
<220> FEATURE:
<223> OTHER INFORMATION: Primer INSP085-exon3R

<400> SEQUENCE: 20
ttagcgtttg ttacctgggt tatgac                                         26

<210> SEQ ID NO 21
<211> LENGTH: 35
<212> TYPE: DNA
<213> ORGANISM: Artificial Sequence
<220> FEATURE:
<223> OTHER INFORMATION: Primer INSP085-EX1

<400> SEQUENCE: 21
gcaggcttcg ccaccatgag cttggctatc ctcat                               35
```

<210> SEQ ID NO 22
<211> LENGTH: 35
<212> TYPE: DNA
<213> ORGANISM: Artificial Sequence
<220> FEATURE:
<223> OTHER INFORMATION: Primer INSP085-EX2

<400> SEQUENCE: 22
gtgatggtga tggtggcgtt tgttacctgg gttat                    35

<210> SEQ ID NO 23
<211> LENGTH: 20
<212> TYPE: DNA
<213> ORGANISM: Artificial Sequence
<220> FEATURE:
<223> OTHER INFORMATION: Primer pEAK12-F

<400> SEQUENCE: 23
gccagcttgg cacttgatgt                                     20

<210> SEQ ID NO 24
<211> LENGTH: 20
<212> TYPE: DNA
<213> ORGANISM: Artificial Sequence
<220> FEATURE:
<223> OTHER INFORMATION: Primer pEAK12-R

<400> SEQUENCE: 24
gatggaggtg gacgtgtcag                                     20

<210> SEQ ID NO 25
<211> LENGTH: 25
<212> TYPE: DNA
<213> ORGANISM: Artificial Sequence
<220> FEATURE:
<223> OTHER INFORMATION: Primer pENTR-F

<400> SEQUENCE: 25
tcgcgttaac gctagcatgg atctc                               25

<210> SEQ ID NO 26
<211> LENGTH: 24
<212> TYPE: DNA
<213> ORGANISM: Artificial Sequence
<220> FEATURE:
<223> OTHER INFORMATION: Primer pENTR-R

<400> SEQUENCE: 26
gtaacatcag agattttgag acac                                24

<210> SEQ ID NO 27
<211> LENGTH: 20
<212> TYPE: DNA
<213> ORGANISM: Artificial Sequence
<220> FEATURE:
<223> OTHER INFORMATION: Primer T7

<400> SEQUENCE: 27
taatacgact cactataggg                                     20

<210> SEQ ID NO 28
<211> LENGTH: 21
<212> TYPE: DNA
<213> ORGANISM: Artificial Sequence
<220> FEATURE:
<223> OTHER INFORMATION: Primer T3

-continued

```
<400> SEQUENCE: 28
ctccctttag tgagggtaat t                                             21
```